(12) United States Patent
Calderone, III

(10) Patent No.: US 11,169,117 B2
(45) Date of Patent: Nov. 9, 2021

(54) METHODS TO ANALYZE HYDROCARBON SOLUTIONS

(71) Applicant: Afton Chemical Corporation, Richmond, VA (US)

(72) Inventor: Joseph Anthony Calderone, III, Powhatan, VA (US)

(73) Assignee: Afton Chemical Corporation, Richmond, VA (US)

( * ) Notice: Subject to any disclaimer, the term of this patent is extended or adjusted under 35 U.S.C. 154(b) by 128 days.

(21) Appl. No.: 16/587,709

(22) Filed: Sep. 30, 2019

(65) Prior Publication Data
US 2021/0096102 A1    Apr. 1, 2021

(51) Int. Cl.
  *G01N 29/02* (2006.01)
  *G01N 33/28* (2006.01)
  *G01N 1/40* (2006.01)
  *G01N 1/38* (2006.01)

(52) U.S. Cl.
  CPC .............. *G01N 29/022* (2013.01); *G01N 1/38* (2013.01); *G01N 1/4022* (2013.01); *G01N 33/28* (2013.01); *G01N 2001/387* (2013.01); *G01N 2001/4027* (2013.01)

(58) Field of Classification Search
  CPC .... G01N 29/022; G01N 33/28; G01N 1/4022; G01N 1/38; G01N 2001/4027; G01N 2001/387; G01N 1/40
  USPC .......... 73/24.01, 24.06, 31.07, 53.01, 61.41, 73/61.49, 61.59, 61.58, 61.75, 64.56, 866; 422/68.1; 585/401, 501, 701
  See application file for complete search history.

(56) References Cited

U.S. PATENT DOCUMENTS

| | | |
|---|---|---|
| 5,661,233 A | 8/1997 | Spates et al. |
| 6,904,786 B2 | 6/2005 | Matsiev et al. |
| 7,204,128 B1 | 4/2007 | Liu et al. |
| 7,293,450 B2 | 11/2007 | Liu et al. |
| 9,581,574 B2 | 2/2017 | Murphy |
| 2012/0160707 A1 | 6/2012 | Kusinski et al. |
| 2012/0160709 A1 | 6/2012 | Kusinski et al. |
| 2012/0160736 A1* | 6/2012 | Kusinski ................. C10L 1/04 208/14 |
| 2012/0166099 A1 | 6/2012 | Kusinski et al. |
| 2013/0303402 A1* | 11/2013 | Warner .................. B01J 20/22 506/12 |
| 2015/0323441 A1 | 11/2015 | Lachance et al. |
| 2019/0257730 A1* | 8/2019 | Parlak .................... G01N 9/002 |

* cited by examiner

*Primary Examiner* — Robert R Raevis
(74) *Attorney, Agent, or Firm* — Honigman LLP

(57) ABSTRACT

The present application describes a method to reduce noise and improve data quality when analyzing hydrocarbon compositions with a Quartz Crystal Microbalance (QCM). In some approaches, the methods described in this disclosure remove at least a portion of volatile components from the hydrocarbon composition to be tested with the QCM.

18 Claims, 15 Drawing Sheets

METHODS TO ANALYZE HYDROCARBON SOLUTIONS

TECHNICAL FIELD

This disclosure is related to compositions and methods to analyze hydrocarbon solutions with a Quartz Crystal Microbalance (QCM). The hydrocarbon solutions can be un-additized, contain an additive, or contain combinations of additives.

BACKGROUND

Many problems encountered in fuel distribution systems and vehicles can be traced back to physical and chemical interactions occurring on surfaces. For example, corrosion is a surface phenomenon where a metal surface undergoes a chemical reaction with molecules in its environment. The resulting corroded metal is not only more prone to mechanical failure but flakes of corroded metal may also contribute to fuel contamination. The effects of wear and friction also occur at the surface, metal on metal contact results in abrasive surface wear and increased coefficients of friction. Excessive wear and high friction contributes to premature engine failure and reduced engine efficiency. Fuel additives such as corrosion inhibitors, antiwear additives, and friction modifiers are capable of mitigating or preventing many of these problems. The QCM provides a method to study the interactions of additives and hydrocarbon fluids, such as gasoline, with metal surfaces.

SUMMARY

Figure 1:
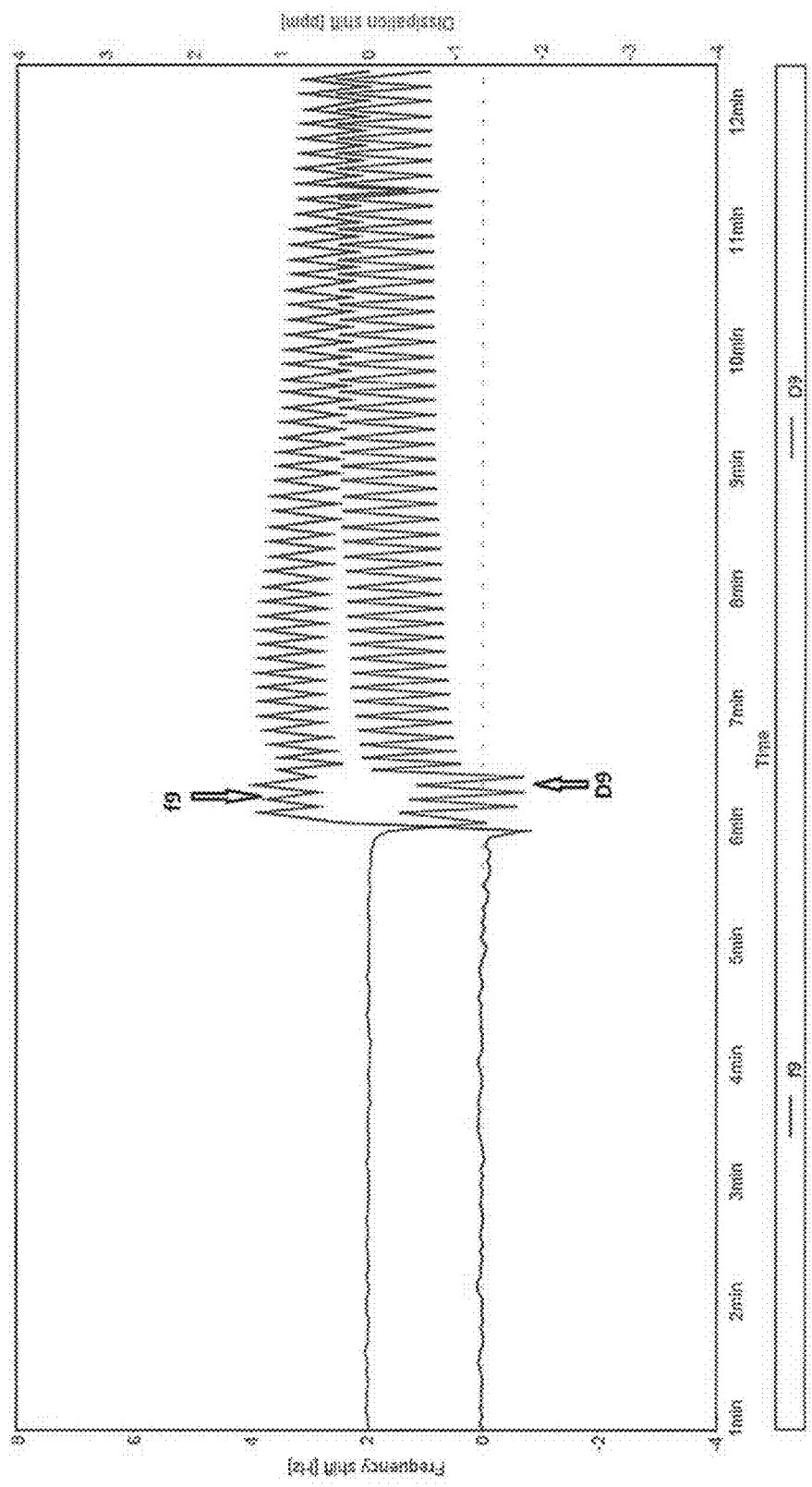
FIGS. 1 to 15 are QCM frequency vs. time plots.

In one approach or embodiment, a method is described to produce a hydrocarbon composition suitable to be run and analyzed with a Quartz Crystal Microbalance (QCM). The hydrocarbon composition has reduced volatility and dissolved gas content. These attributes reduce and/or prevent the formation of gas bubbles in the piping and test cell(s) of the QCM during experiments. The reduction of gas bubbles from forming during QCM experiments is helpful in producing quality data while analyzing hydrocarbon compositions such as gasoline with the QCM instrument.

In another approach or embodiment, one aspect to producing a hydrocarbon composition suitable to be run and analyzed with a QCM is achieved by reducing the concentration of volatile components (such as C5 and lower hydrocarbons) in the hydrocarbon composition to be tested. This can be achieved by several means such as heating the hydrocarbon composition under atmospheric conditions or allowing the hydrocarbon solution to evaporate at atmospheric temperature and pressure. More preferential methods include applying vacuum to the hydrocarbon composition without applying heat or heating the hydrocarbon composition under vacuum. The most preferred method is to bubble a gas or mixture of gases through the hydrocarbon composition to evaporate volatile components.

In another approach or embodiment, another aspect to producing a hydrocarbon composition suitable to be run and analyzed with a QCM is achieved by reducing the concentration of dissolved gases in the hydrocarbon composition. This can be achieved by several means including passing the hydrocarbon composition through an in-line degassing system. More preferably the hydrocarbon solution can be placed under vacuum to remove dissolved gases. The most preferred method is to sparge the hydrocarbon composition with a gas with minimal solubility in the hydrocarbon composition that is still capable of displacing dissolved oxygen and air.

In another approach or embodiment, a hydrocarbon composition suitable to be run and analyzed with a QCM is achieved by reducing the temperature of the QCM test cell and the hydrocarbon solution being analyzed. Reducing the temperature of the hydrocarbon solution and test cell reduces the tendency for gas bubbles to form in the lines and test cell(s) of the QCM.

In yet another approach or embodiment, the suitability for running a specific hydrocarbon composition in a QCM can be assessed by measuring its volatility. Methods to evaluate the volatility of the hydrocarbon solution include quantifying the volatile fractions of the hydrocarbon composition by generating a distillation curve. Alternately the vapor pressure of the hydrocarbon solution can be used to assess volatility.

In yet another approach or embodiment, the starting hydrocarbon composition can consist of gasoline, gasoline blend components, or gasoline simulants. The starting hydrocarbon composition is defined as the hydrocarbon composition prior to being made suitable for use on a QCM. Gasoline is a hydrocarbon composition intended for or suitable for use in an internal combustion engine. Gasoline which can be used in the above mentioned approaches and embodiments can further be a hydrocarbon fluid that meets a government or industry accepted specification for use. For example European motor gasoline generally meets the EN228 specification, and United States motor gasoline generally meets the ASTM D4814 specification, both of which are incorporated herein by reference. Gasoline blend components are the refinery streams blended to create gasoline. Gasoline simulants are hydrocarbons or hydrocarbon solutions, known to those skilled in the art, which are suitable simulants for gasoline.

In another approach or embodiment, a method of determining the surface activity of a hydrocarbon composition on a metal surface is described. In some approaches, this method is suitable to reduce noise and improve data quality when analyzing the hydrocarbon composition with a Quartz Crystal Microbalance (QCM). In some approaches, the method includes (a) treating the hydrocarbon composition by removing at least a portion of volatile components from the hydrocarbon composition to form a treated hydrocarbon composition; and (b) measuring the frequency of oscillation of the treated hydrocarbon fluid on a metal surface by quartz crystal microbalance.

The method as described in the previous paragraph may be combined with one or more optional features in any combination. These additional embodiments of the method may each include such optional features in any combination and may include: wherein the portion of the volatile components in the hydrocarbon composition is reduced by bubbling a gas through the hydrocarbon composition; and/or wherein the gas is selected from an inert or a noble gas; and/or wherein the gas includes nitrogen, helium, argon, air, oxygen, or a combination thereof; and/or wherein the gas is bubbled through the hydrocarbon composition for at least 10 minutes, at least 30 minutes, at least 60 minutes, at least 90 minutes; and/or wherein the gas is bubbled through the hydrocarbon composition for a time sufficient to reduce bubble formation in the QCM; and/or wherein the gas is bubbled through the hydrocarbon composition for a time sufficient to reduce the volatile components in the hydrocarbon composition when measured using the ASTM D86 distillation method; and/or wherein the gas is bubbled through the hydrocarbon composition for a time sufficient to reduce the mass of the hydrocarbon composition; and/or wherein the gas is bubbled through the hydrocarbon composition for a time sufficient to reduce frequency spikes and reduce noise spikes occurring in the analysis of the second hydrocarbon composition with the QCM; and/or wherein the volatile components are removed by allowing the hydrocarbon composition to evaporate at atmospheric pressure; and/or wherein the evaporation of the hydrocarbon composition is sufficient to reduce the volatile components in the hydrocarbon composition when measured using the ASTM D86 distillation method; and/or wherein the evaporation of the hydrocarbon composition is sufficient to reduce the mass of the hydrocarbon composition; and/or wherein the evaporation of the hydrocarbon composition is sufficient to reduce frequency spikes and reduce noise spikes occurring in the analysis of the second hydrocarbon composition with the QCM; and/or wherein the volatile components are removed by distilling the light ends of the hydrocarbon composition; and/or wherein the distilling includes rotary evaporation; and/or wherein the distillation of hydrocarbon composition is sufficient to reduce the volatile components in the hydrocarbon composition when measured using the ASTM D86 distillation method; and/or wherein the distillation of the hydrocarbon composition is sufficient to reduce the mass of the hydrocarbon composition; and/or wherein the distillation of the hydrocarbon composition is sufficient to reduce frequency spikes and reduce noise spikes occurring in the analysis of the second hydrocarbon composition with the QCM; and/or further including removing at least a portion of any dissolved gas by degassing the second hydrocarbon composition; and/or wherein the degassing is through helium sparging, vacuum degassing, and/or inline degassing; and/or wherein the hydrocarbon composition is gasoline, an E0 to an E85 gasoline, a gasoline simulant, an EN 228 compliant gas, and/or standard test fuel or reference fuel, and/or combinations thereof; and/or wherein the hydrocarbon composition includes one or more of reformate, alkylate, FCC, straight run gasoline, or isomerate; and/or wherein the volatile components include C5 or lower hydrocarbons; and/or wherein the hydrocarbon composition includes one or more additives selected from the group consisting of metallic octane boosters, organometallic octane boosters, organic octane boosters, pre-ignition preventers, detergents, dispersants, injector cleanliness additives, corrosion inhibitors, markers, demulsifiers, solvents, carrier fluids, conductivity improvers, cold flow improvers, combustion improvers, friction modifiers, antiwear additives, valve seat recession additives, wax inhibitors, and combinations thereof.

DETAILED DESCRIPTION

Significant advances have been made in QCM technology in the past sixty years. The technology was initially developed to study the interactions of gas molecules on surfaces but it was later adapted to operate in liquids. QCM technology has been engineered and simplified such that it is no longer highly specialized technology but something available to increasing numbers of universities and corporations. With applications in fields ranging from biology to nanoscience, QCM technology is a helpful analytical tool to study the interaction of surface-active materials with surfaces.

Chemical and physical interactions occurring on the surfaces of fuel distribution and storage systems as well as in vehicles can explain many of the problems or challenges observed in the field. Corrosion involves the chemical modification of a metal surface. Contact of the metal surface with water, particularly salt water, increases corrosion. Similarly contact of the metal surface with aqueous solutions of high or low pH will also accelerate corrosion. Corrosion weakens metals and in severe cases can lead to rupture of metal pipelines and storage tanks. Friction and wear, responsible for reduced engine efficiency and premature component failure results from the contact of two metal surfaces with a load applied to one or both of the metal surfaces. Low lubricity fuel has been implicated in causing increased pump failures in both turbine engines and compression ignition engines due to increased pump wear. Engine deposits, in the form of injector deposits, intake valve deposits, or combustion chamber deposits result from carbonaceous combustion products adhering to engine surfaces. The presence of these deposits can reduce engine efficiency, harm emissions, and in severe cases lead to pre-ignition or poor combustion.

The inherent properties of the fuel as well as the presence of fuel additives can prevent or mitigate many of the abovementioned problems. For example, legislation to reduce the sulfur content in middle distillates unintentionally reduced the concentration of surface active molecules which provided these fuels their inherent lubricity. Surface active lubricity improvers are now added to middle distillates to prevent wear and excessive friction. Gasoline also contains surface active molecules responsible for the inherent lubricity of gasoline. To further reduce wear and friction in spark ignited engines, lubricity improvers and friction modifiers are added to gasoline. These lubricity improvers are commonly designed with a polar head group, which binds to the metal surface and a non-polar tail, which increases the lubricity of the fuel. Likewise, detergent molecules are designed with polar headgroups and nonpolar tails in order to adhere to metal surfaces or deposits. When bound to a metal surface, the detergent prevents deposits from forming. When bound to a deposit, the detergent is capable of removing the deposit from a metal surface.

A QCM is a useful tool for studying the interactions of fuels and additives with surfaces. However, QCM technology is better suited for studying aqueous systems such as those encountered in life science applications. Materials compatibility along with the volatility of hydrocarbons makes their analysis with QCM problematic. The volatile components of hydrocarbon compositions such as gasoline tend to form gas bubbles in the lines and test cell(s) of the QCM. The presence of these bubbles can significantly reduce signal quality, sometimes to the extent that the data cannot be interpreted. Materials compatibility poses another challenge as QCM components designed to be compatible with aqueous media are often incompatible with hydrocarbons.

With this background, the present disclosure relates to compositions and methods to analyze hydrocarbon solutions using a QCM. Several approaches describe methods to reduce the concentration of volatile components in the hydrocarbon composition to a level that is suitable for QCM analysis. In one such approach, a gas such as nitrogen is bubbled through the hydrocarbon solution for a sufficient time to evaporate off the volatile components. Further embodiments of the disclosure herein describe alternate methods to produce a hydrocarbon composition suitable for QCM analysis. In another aspect, hydrocarbon compositions suitable for QCM analysis are defined based on their volatility.

The Quartz Crystal Microbalance:

In one aspect of this disclosure, a Quartz Crystal Microbalance is used to study the mass of surface active species present in hydrocarbon solutions that adsorbs to a surface. QCM sensor discs consist of an AT- or SC-cut of quartz or any other material, which will exhibit a shear resonance ranging from 1-30 MHz when an electric current is applied. Discs capable of shear resonance in the 1-10 MHz range are preferred. Discs capable of shear resonance in the 4-8 MHz range are more preferred. Portions of the sensor disc are coated with a gold electrode and counter electrode but other conductive materials suitable to serve as electrodes fall within the scope of this disclosure.

The side of the QCM disc with the electrodes shall be referred to as the electrode side while the side of the QCM disc in contact with the gas or liquid to be analyzed will be referred to as the sensor side. The sensor side of the QCM disc can consist of quartz or similar material capable of shear resonance in the 1-30 MHz range. Optionally, the sensor side of the disc can be coated with one or more materials. One example of such materials is metals which include but are not limited to gold, titanium, tantalum, platinum, iridium, and iron, or combinations thereof. Metal coatings capable of being deposited on the sensor side of the disc through resistive evaporation or sputtering fall within this disclosure. Another such example of such materials is alloys which include but are not limited to stainless steel, carbon steel, aluminum alloys, brass, bronze, Monel, or Hastelloy, or combinations thereof. Alloys of stainless steel are a preferred embodiment of this disclosure. Stainless steel 304 and stainless steel 316 are more preferred embodiments of this disclosure. Stainless steel that meets Swedish grade 2343 is most preferred. Additional alloys capable of being deposited on the surface of the sensor side of the disc through sputtering or other common atomic layer deposition or chemical vapor deposition techniques fall within the scope of this disclosure. Chemical compounds may be deposited on the sensor side of the disc. Non-limiting examples include oxides, halides, nitrides, nitrates, sulfides, sulfates, or combinations thereof. Aluminum oxide and iron oxide are preferred examples of oxides. Glasses, ceramics, and refractory materials may be deposited on the sensor side of the disc as well. Organic or carbon based materials can be deposited on the sensor side of the disc. Preferred examples include polystyrene, polypropylene, polybutylene, polyethylene, or combinations thereof. Examples of carbon based materials include charcoal and graphite. More preferred examples are Diamond Like Coatings (DLCs), graphene, carbon nanotubes, and fullerenes. Carbonaceous combustion depositions, including but not limited to soot, are most preferred examples. Each of the above materials may be present on the sensor side of the disc by itself or in combination with one or more other material(s).

The QCM instrument consists of several components; a test cell or vessel that holds the QCM disc, an electronics system responsible for making the QCM disc oscillate, a temperature control system, and a data acquisition system. The test cell or vessel that holds the QCM disc in such a manner that the sensor side of the disc contacts the liquid or gas being analyzed. The liquid or gas may be introduced and held statically in the test or cell or vessel but it is preferred the liquid or gas is flowed through the test cell or vessel. In a more preferred embodiment, sufficiently chemical resistant tubing, such as PTFE tubing, along with a peristaltic pump is used to pull fluid through the test cells of the QCM instrument. In a preferred embodiment, an apparatus to bubble a gas capable of sparging dissolved air from the hydrocarbon composition is present such as before the test cell. Preferred gases are inert gases with low solubility in hydrocarbon solutions. Preferred examples are nitrogen, argon, and helium. This apparatus consists of a gas tank, a pressure regulator, tubing, and needles, or similar means, of bubbling the gas through the hydrocarbon solution. The electronics system making the disc oscillate should be sufficient to make the QCM disc oscillate with a shear resonance ranging from 1-30 MHz. More preferably, the electronics system should be capable of oscillating the discs with a shear frequency ranging from 1-10 MHz. Most preferably, the electronics system should be capable of oscillating the discs with a shear frequency ranging from 4-8 MHz. The temperature control system should be capable of maintaining a controlled temperature in the test cell or vessel. Suitable temperatures to run experiments range from −20° to 75°. In other approaches, temperatures range from −20° C. to −10° C., −10 to 0° C., 0° C. to 10° C., 10° C. to 20° C., 20° C. to 25° C., 25° C. to 35° C., 35° C. to 45° C., or 45° C. to 75° C. Preferred embodiments have temperatures from 10° C. to 20° C. or 25° C. to 35° C., temperatures ranging from 20° C. to 25° C. are most preferred. The data acquisition system should be capable of outputting one or more of the following measurements: temperature, time, frequency (or frequency change), and dissipation (or dissipation change). It is preferred all four measurements are acquired during an experiment. Logging frequency change as a function of time allows for the Sauerbrey Equation to be used to determine adsorbed mass as a function of time. Changes in adsorbed mass provide insight into the interactions of different hydrocarbon solutions and/or fuel additives of the hydrocarbon solution with surfaces. Dissipation is a measure of energy loss when the electric current to the disc is briefly stopped. As the QCM disc dissipates energy, its oscillation frequency begins to decay. The rate of oscillation frequency decay may depend on one or more factors, the size, mass, type, or organization of the surface film. Dissipation and frequency can optionally be used together to perform viscoelastic modelling of the adsorbed surface film. Preferred viscoelastic models are the Voight and Maxwell models.

Applicable Starting Hydrocarbon Compositions:

Starting hydrocarbon compositions are those which can be converted into hydrocarbon compositions suitable for QCM experiments. A hydrocarbon composition may be a liquid, including, consisting essentially of, or consisting of at least one or more compound(s) or molecule(s) predominantly composed of the elements hydrogen, carbon, and oxygen. In embodiments of this disclosure the sum of carbon, oxygen, and hydrogen sum to at least 90% of the composition, more preferably at least 95% of the composition, or even more preferably at least 99% of the composition, or most preferably sum to at least 99.9% of the composition. The percentage of carbon, oxygen, and hydrogen can be determined on a mass, volume, molar, or atomic percentage basis. Other nonmetals may optionally be present, for example sulfur, phosphorous, and nitrogen. Common sources of compounds containing carbon, oxygen, nitrogen, sulfur, phosphorous and hydrogen are organic compounds. Non-limiting examples of these compounds include alkanes, cycloalkanes, alkenes, cycloalkenes, alkynes, cycloalkynes, aromatics, polyaromatics, alcohols, ethers, esters, epoxides, aldehydes, ketones, carboxylic acids, anhydrides, oxygen containing heterocyclic compounds, amides, amines, nitriles, imines, isocyanates, nitrogen containing heterocyclic compounds, thiols, thioesters, thioethers, disulfides, sulfur containing heterocyclic compounds, phosphates, phosphines, phosphites, phosphorous containing heterocyclic compounds, and combinations thereof. Compounds or molecules which fall under the description of organophosphorous or organosulfur compounds fall under this invention. As do compounds or molecules which contain carbon-carbon, carbon-oxygen, carbon-nitrogen, carbon-sulfur, carbon-phosphorous, or carbon-hydrogen bonds. Trace amounts of halogens, semimetals, basic metals, transition metals, alkali metals, and alkaline metals may also be present. Preferred examples of such trace elements are iron, nickel, vanadium, sodium, copper, aluminum, calcium, silicon, magnesium, and potassium. The majority of the hydrocarbon composition will not contain water. Water may be optionally present up to 10 vol %, 5 vol %, 3 vol %, 1 vol %, or more preferably trace levels. Aqueous solutions do not fall under the definition of hydrocarbon compositions. Molecules or compounds, which may not be considered a part of the starting hydrocarbon composition, may be included as well. One such example are fuel additives such as metallic octane boosters, organometallic octane boosters, organic octane boosters, pre-ignition preventers, detergents, dispersants, injector cleanliness additives, corrosion inhibitors, markers, demulsifiers, solvents, carrier fluids, conductivity improvers, cold flow improvers, combustion improvers, friction modifiers, antiwear additives, valve seat recession additives, and wax inhibitors, and combinations thereof. These molecules are typically present at parts per million concentrations but may be present up to 2% in the hydrocarbon composition. One exception to this is organic octane boosters, which may be present in concentrations ranging from 0.1% to 1%, 1% to 3%, 3% to 5%, or 5% to 10%. The percentage of additive present may be calculated on a mass or volume percent basis.

In one embodiment, a suitable starting hydrocarbon composition is gasoline simulants. Gasoline simulants approximate the physical properties and combustion behavior of gasoline but contain fewer components. Gasoline are considered hydrocarbon compositions for this disclosure. Gasoline simulants consist of least one but optionally mixtures of alkanes, cycloalkanes, aromatics, napthalenes, or olefins. Oxygenates may be included in the hydrocarbon composition as well. Examples of oxygenates include but are not limited to alcohols, ethers, esters, carbonates, or oxygen containing heterocycles. Preferred examples of gasoline simulants are Primary Reference Fuels, which comprise, consist essentially of, or consist of mixtures of iso-octane, n-heptane, and optionally toluene. For QCM experiments, iso-octane is a particularly preferred gasoline simulant. Another preferred embodiment of this disclosure is mixtures of iso-octane and ethanol. Ethanol can be added to iso-octane in quantities ranging from 0.5 vol % to 99.5 vol %. Preferred mixtures of ethanol in iso-octane range from 50 vol % to 85 vol %, 30 vol % to 40 vol %, and 20 vol % to 30 vol %. More preferred mixtures contain 11 vol % to 20 vol %, most preferred embodiments contain 1 vol % to 11 vol % ethanol.

In another embodiment, the starting hydrocarbon composition comprises, consists essentially of, or consists of at least one but optionally mixtures of refinery blend components. Refinery blend components, produced from a crude oil or similar feedstock, are used to blend finished fuels. Non-limiting examples of refinery blend components include isomerate, reformate, hydrocracked gasoline, straight run gasoline, alkylate, fluid catalytic cracked (FCC) gasoline, and coker naptha, and combinations thereof. Other refinery blend components used to produce motor gasoline, aviation gasoline, on-road and off-road diesel fuel, and turbine fuel fall within the scope of this invention. Preferred examples of mixtures of refinery components are hydrocarbon compositions which meet the specifications and physical properties of Conventional Blendstock for Oxygenate Blending (CBOB) gasoline, Reformulated Blendstock for Oxygenate Blending (RBOB) gasoline, or California Reformulated Blendstock for Oxygenate Blending (CARBOB) gasoline. Fuel additives may be present in the refinery blend components or combinations of refinery blend components. Examples of such fuel additives include metallic octane boosters, organometallic octane boosters, organic octane boosters, pre-ignition preventers, detergents, dispersants, injector cleanliness additives, corrosion inhibitors, markers, demulsifiers, solvents, carrier fluids, conductivity improvers, cold flow improvers, combustion improvers, friction modifiers, antiwear additives, valve seat recession additives, and wax inhibitors, and mixtures thereof. These molecules are typically present at parts per million concentrations but may be present up to 2% in the composition. One exception to this is organic octane boosters, which may be present in concentrations ranging from 0.1% to 1%, 1% to 3%, 3% to 5%, or 5% to 10%. The percentage of additive present may be calculated on a mass or volume percent basis.

In yet another embodiment, the starting hydrocarbon composition is a finished fuel. A finished fuel is suitable for use in an internal combustion engine or turbine engine. Non-limiting examples of internal combustion or turbine engines include spark ignited engines, compression ignited engines, homogenous charge compression ignition engines, Atkinson-cycle engines, Otto-cycle engines, 2-stroke engines, 4-stroke engines, and Brayton-cycle engines. Finished fuels suitable for internal combustion engines and turbine engines include gasoline, diesel fuel, and kerosene. Preferred examples of such fuels include motor gasoline, aviation gasoline, on-road diesel, off-road diesel, marine-diesel, home heating oil, and jet fuel. In a preferred embodiment of this invention the starting hydrocarbon composition is a finished fuel meeting a governmental or industry standard specification for physical properties, quality, composition, characteristics, or end use. For example, United States motor gasoline which meets the ASTM D4814 Standard Specification for Automotive Spark-Ignition Engine Fuel is a preferred starting hydrocarbon composition. European motor gasoline which meets the DIN EN228 Automotive Fuels—Unleaded Petrol—Requirements and Test Methods is another preferred starting hydrocarbon composition. Gasoline can be oxygenate free, known as E0 gasoline, or contain oxygenates. While many oxygen containing classes of molecules such as esters, ketones, ethers, alcohols, aldehydes, and furans qualify as oxygenates, preferred examples of oxygenates include methyl t-butyl ether (MTBE), ethyl t-butyl ether (ETBE), methanol, and ethanol. In one aspect, oxygenates can be blended into gasoline ranging from 1 vol % to 99 vol %. Preferred gasoline oxygenate blends include 5 vol %, 10 vol %, 15 vol %, 20 vol %, 30 vol %, or 85 vol %. Preferred ethanol-gasoline blends include E0, E5, E10, E15, E20, E25, E30, or E85. Gasoline can be either summer or winter blends or Reformulated Gasoline (RFG). In another embodiment, certification fuels, test fuels, and experimental fuels are starting hydrocarbon compositions. Examples of these fuels include Tier II EEE gasoline, Tier III EEE gasoline, Euro Stage IV gasoline, or Euro Stage V gasoline. Finished fuels may contain or be free of additives. Examples of such additives include but are not limited to metallic octane boosters, organometallic octane boosters, organic octane boosters, pre-ignition preventers, detergents, dispersants, injector cleanliness additives, corrosion inhibitors, markers, demulsifiers, solvents, carrier fluids, conductivity improvers, cold flow improvers, combustion improvers, friction modifiers, antiwear additives, valve seat recession additives, or wax inhibitors, and combinations thereof. These molecules are typically present at parts per million concentrations but may be present up to 2% in the composition. One exception to this is organic octane boosters, which may be present in concentrations ranging from 0.1% to 1%, 1% to 3%, 3% to 5%, or 5% to 10%. The percentage of additive present may be calculated on a mass or volume percent basis.

Other Additives:

One or more optional compounds may be present in the hydrocarbon or fuel compositions of the disclosed embodiments. For example and in addition to the other additives discussed above, the fuels and/or hydrocarbon compositions herein may contain conventional quantities of cetane improvers, octane improvers, corrosion inhibitors, cold flow improvers (CFPP additive), pour point depressants, solvents, demulsifiers, lubricity additives, friction modifiers, amine stabilizers, combustion improvers, detergents, dispersants, antioxidants, heat stabilizers, conductivity improvers, metal deactivators, marker dyes, organic nitrate ignition accelerators, cycloaromatic manganese tricarbonyl compounds, carrier fluids, and the like, and various mixtures thereof. In some aspects and unless otherwise noted above, the compositions described herein may contain about 2 weight percent or less, or in other aspects, about 1 weight percent or less, based on the total weight of the hydrocarbon composition, of one or more of the above additives. Similarly, the fuels may contain suitable amounts of conventional fuel blending components such as methanol, ethanol, dialkyl ethers, 2-ethylhexanol, and the like.

In some aspects of the disclosed embodiments, organic nitrate ignition accelerators that include aliphatic or cycloaliphatic nitrates in which the aliphatic or cycloaliphatic group is saturated, and that contain up to about 12 carbons may be used. Examples of organic nitrate ignition accelerators that may be used are methyl nitrate, ethyl nitrate, propyl nitrate, isopropyl nitrate, allyl nitrate, butyl nitrate, isobutyl nitrate, sec-butyl nitrate, tert-butyl nitrate, amyl nitrate, isoamyl nitrate, 2-amyl nitrate, 3-amyl nitrate, hexyl nitrate, heptyl nitrate, 2-heptyl nitrate, octyl nitrate, isooctyl nitrate, 2-ethylhexyl nitrate, nonyl nitrate, decyl nitrate, undecyl nitrate, dodecyl nitrate, cyclopentyl nitrate, cyclohexyl nitrate, methylcyclohexyl nitrate, cyclododecyl nitrate, 2-ethoxyethyl nitrate, 2-(2-ethoxyethoxy)ethyl nitrate, tetrahydrofuranyl nitrate, and the like. Mixtures of such materials may also be used.

Examples of suitable optional metal deactivators useful in the compositions of the present application are disclosed in U.S. Pat. No. 4,482,357, the disclosure of which is herein incorporated by reference in its entirety. Such metal deactivators include, for example, salicylidene-o-aminophenol, disalicylidene ethylenediamine, disalicylidene propylenediamine, and N,N'-disalicylidene-1,2-diaminopropane.

Suitable optional cycloaromatic manganese tricarbonyl compounds which may be employed in the compositions of the present application include, for example, cyclopentadienyl manganese tricarbonyl, methylcyclopentadienyl manganese tricarbonyl, indenyl manganese tricarbonyl, and ethylcyclopentadienyl manganese tricarbonyl. Yet other examples of suitable cycloaromatic manganese tricarbonyl compounds are disclosed in U.S. Pat. Nos. 5,575,823 and 3,015,668, both of which are incorporated by reference in their entirety.

Other commercially available detergents and/or additives may be used in combination with the reaction products described herein. Such detergents include but are not limited to succinimides, Mannich base detergents, quaternary ammonium compounds, bis-aminotriazole detergents as generally described in U.S. patent application Ser. No. 13/450,638, and a reaction product of a hydrocarbyl substituted dicarboxylic acid, or anhydride and an aminoguanidine, wherein the reaction product has less than one equivalent of amino triazole group per molecule as generally described in U.S. patent application Ser. Nos. 13/240,233 and 13/454,697.

The additives of the present application, and any optional additives used in formulating the fuels of this disclosure may be blended into a base fuel individually or in various sub-combinations. In some embodiments, the additive components of the present application may be blended into the fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

Base Fuels:

The hydrocarbon compositions of the present application may be a base fuel or base hydrocarbon fuel applicable to the operation of diesel, jet, or gasoline engines. In one approach, the fuels or hydrocarbon compositions herein are well suited for diesel or gasoline and, particularly, gasoline. In one embodiment, the fuel is gasoline. In other another embodiment, the fuel is a diesel. The fuels may include any and all middle distillate fuels, diesel fuels, biorenewable fuels, biodiesel fuel, fatty acid alkyl ester, gas-to-liquid (GTL) fuels, gasoline, jet fuel, alcohols, ethers, kerosene, low sulfur fuels, synthetic fuels, such as Fischer-Tropsch fuels, liquid petroleum gas, bunker oils, coal to liquid (CTL) fuels, biomass to liquid (BTL) fuels, high asphaltene fuels, fuels derived from coal (natural, cleaned, and petcoke), genetically engineered biofuels and crops and extracts therefrom, and natural gas. "Biorenewable fuels" as used herein is understood to mean any fuel which is derived from resources other than petroleum. Such resources include, but are not limited to, corn, maize, soybeans and other crops; grasses, such as switchgrass, miscanthus, and hybrid grasses; algae, seaweed, vegetable oils; natural fats; and mixtures thereof. In an aspect, the biorenewable fuel can comprise monohydroxy alcohols, such as those comprising from 1 to about 5 carbon atoms. Non-limiting examples of suitable monohydroxy alcohols include methanol, ethanol, propanol, n-butanol, isobutanol, t-butyl alcohol, amyl alcohol, isoamyl alcohol, and mixtures thereof. Preferred fuels include gasoline fuels.

The fuels or hydrocarbon compositions herein are suitable for use in various internal combustion systems or engines. The systems or engines may include both stationary engines (e.g., engines used in electrical power generation installations, in pumping stations, etc.) and ambulatory engines (e.g., engines used as prime movers in automobiles, trucks, road-grading equipment, military vehicles, etc.). By combustion system or engine herein is meant, internal combustion engines, for example and not by limitation, Atkinson cycle engines, rotary engines, spray guided, wall guided, and the combined wall/spray guided direct injection gasoline ("DIG" or "GDI") engines, turbocharged DIG engines, supercharged DIG engines, homogeneous combustion DIG engines, homogeneous/stratified DIG engines, DIG engines outfitted with piezoinjectors with capability of multiple fuel pulses per injection, DIG engines with EGR, DIG engines with a lean-NOx trap, DIG engines with a lean-NOx catalyst, DIG engines with SN-CR NOx control, DIG engines with exhaust diesel fuel after-injection (post combustion) for NOx control, DIG engines outfitted for flex fuel operation (for example, gasoline, ethanol, methanol, biofuels, synthetic fuels, natural gas, liquefied petroleum gas (LPG), and mixtures thereof.) Also included are conventional and advanced port-fueled internal combustion engines, with and without advanced exhaust after-treatment systems capability, with and without turbochargers, with and without superchargers, with and without combined supercharger/turbocharger, with and without on-board capability to deliver additive for combustion and emissions improvements, and with and without variable valve timing. Further included are gasoline fueled homogeneous charge compression ignition (HCCI) engines, diesel HCCI engines, two-stroke engines, diesel fuel engines, gasoline fuel engines, stationary generators, gasoline and diesel HCCI, supercharged, turbocharged, gasoline and diesel direct injection engines, engines capably of variable valve timing, leanburn engines, engines capable of inactivating cylinders or any other internal combustion engine. Still further examples of combustion systems include any of the above-listed systems combined in a hybrid vehicle with an electric motor.

Methods to Prepare Hydrocarbon Compositions Suitable for QCM Experiments:

Another aspect of this disclosure is methods to reduce the volatility of the starting hydrocarbon composition to a level that it is suitable for analysis with the QCM. In one aspect of the preparation methods, the hydrocarbon composition is modified by first removing at least a portion of the volatile components, such as but not limited to, C5 and lower hydrocarbons. The amount of volatile components removed can be assessed by measuring the mass of the hydrocarbon composition prior to and after the removal of the volatile components. Distillation can be alternately used to assess how much volatile components have been removed. Alternately compositional hydrocarbon analysis by methods such as but not limited to gas chromatography can be used.

In one approach, the hydrocarbon solution or composition is allowed to evaporate to remove the volatile components. Evaporation may be performed, for example, at atmospheric pressures and either at ambient or slightly elevated temperature. Ambient temperatures (15° C. to 38° C.) are preferred. In some approaches, care must be taken when using elevated temperatures, 39° C. to 50° C., to avoid igniting the hydrocarbon solution. In this approach, the hydrocarbon solution is placed in a vessel that is open to the atmosphere. Preferably, the vessel is placed in a ventilated environment with low exposure to sunlight. The hydrocarbon solution may be allowed to evaporate for 1 hour up to 96 hours. Preferable evaporating times are 1-3 hours, 3-5 hours, 5-8 hours, or 8-12 hours. Less preferable evaporation times are 12-18 hours, 18-24 hours, 24-48 hours, 48-72 hours, or 72-96 hours. Optionally, the hydrocarbon composition may be stirred or otherwise agitated while evaporating.

While effective, evaporating under ambient atmosphere can be time consuming and increase the risk for hydrocarbon composition oxidation due to prolonged contact with the air. In another approach, evaporation may occur with a gas bubbled through the hydrocarbon composition to speed evaporation of the volatile components. Preferably, the bubbling gas is an inert gas, such as nitrogen, helium, or argon, or combinations thereof. In other cases, the gas may be air, oxygen, or combinations thereof. Employing an inert gas both speeds evaporation and prevents oxidation of the hydrocarbon solution. In this approach, a system to supply the inert gas into a vessel containing a hydrocarbon composition is employed. The inert gas supply can come from a gas cylinder or be supplied by the facility, for example "house nitrogen." A valve or regulator is used to control the flow rate of the gas into the hydrocarbon solution. Chemically inert tubing, and optionally a needle, is used to supply the gas into the hydrocarbon solution. If employed the size of the needle can range from 10 gauge to 33 gauge, preferably, the size of the needle is less than 18 gauge. The diameter of the gas supply line into the hydrocarbon composition is at least 0.10 mm, preferably greater than 0.5 mm, or more preferably at least 1 mm in diameter. Preferably, this apparatus and vessel are in a ventilated environment with low exposure to sunlight. Gas is bubbled into the hydrocarbon composition at such a rate to produce a consistent stream of bubbles in the hydrocarbon composition but not too fast to produce splashing of the hydrocarbon composition. The bubbling time varies but can range from 15 minutes up to 24 hours. For example, bubbling times can range from 15-30 minutes, 30-45 minutes, 45-60 minutes, 60-90 minutes, or 90-120 minutes. In other examples the bubbling time can be 2-4 hours, 4-6 hours, 6-8 hours, 8-10 hours, 10-16 hours, 16-20 hours, or 20-24 hours. Shorter bubbling times ranging from 15 minutes to 4 hours is preferred. Optionally, the hydrocarbon composition may be stirred or otherwise agitated.

In yet another approach, the volatility of the starting hydrocarbon composition is reduced by evaporation and/or optionally applying a vacuum to the solution at either ambient or elevated temperatures. Distillation is one such example of a suitable method to remove the volatile components of a hydrocarbon composition by evaporation. Examples of distillations include but are not limited to simple distillation, fractional distillation, vacuum distillation, steam distillation, and short path distillation. Applicable distillation techniques are described in Organic Chemistry Lab Techniques by Lisa Nichols, which is incorporated herein by reference. In one example, a simple distillation is performed under an inert gas atmosphere. Heat is applied to a vessel containing the hydrocarbon composition; the vessel is equipped with a distillation head and condenser to facilitate the removal of volatile components into a collection vessel. In another example, a vacuum distillation, a vacuum is applied to the distillation apparatus consisting of the vessel containing hydrocarbon composition, still head, condenser, and collection vessel. In a preferred example volatile components present in the hydrocarbon composition are removed under rotary evaporation using a rotovap instrument. Collection fractions of distillations of hydrocarbon compositions performed using the ASTM D86 (included herein by reference) Standard Test Method for Distillation of Petroleum Products and Liquid Fuels at Atmospheric Pressure or similar methods fall within the scope of this disclosure.

In another approach, methods to remove dissolved air or other gases may also be completed in addition to or in place of the evaporation discussed above. For instance, dissolved air or gas may be removed from the hydrocarbon compositions after the evaporation and immediately prior to their analysis by the QCM. In starting hydrocarbon compositions and in hydrocarbon compositions that have had their volatile components removed, air or other gas can become dissolved in the solution. This dissolved air or gas can lead to undesired bubble formation inside of the QCM during experiments. One preferred method to remove dissolved air or gas from the hydrocarbon composition or an evaporated hydrocarbon composition is to sparge the solution with an inert gas that is capable of displacing dissolved air/gas but has low solubility itself in the hydrocarbon solution. One such sparging gas is helium. In the context of this disclosure, sparging is different from evaporating (discussed above) in that the sparging time is significantly shorter than the bubbling time used to evaporate volatile components. The sparging time can range from 1 minute to 10 minutes; preferably, the sparging time is either 1-2 minutes or 2-4 minutes. Furthermore, lower pressures or flow rates of gas are required for sparging compared to evaporating volatile components. Unlike evaporating, sparging should not significantly alter the material composition of the hydrocarbon composition. One example of a suitable sparging apparatus consists of a cylinder supplying a sparging gas, a regulator to control pressure and flow, tubing and a needle to introduce gas into the hydrocarbon solution. The preferred size of the needle is 18 gauge or smaller. If a needle is not employed the diameter of the sparging gas delivery line may be less than 1 mm, less than 0.5 mm, or less than 0.1 mm. Alternate methods to remove dissolved air from the hydrocarbon composition can be employed; one non-limiting example is an in-line degassing system.

Hydrocarbon Compositions Suitable for QCM Experiments:

The above methods produce hydrocarbon compositions suitable for the use in a QCM. The compositions may be prepared by the above described evaporation, sparging, or combinations (in any order.) Preferably, the compositions are first evaporated and then sparged. The physical properties of these hydrocarbon compositions can be assessed by several means. The Reid Vapor Pressure (RVP) is one such method; another particularly useful method is to determine the boiling range of the suitable hydrocarbon composition through distillation. The ASTM D86 Standard Test Method for Distillation of Petroleum Products and Liquid Fuels at Atmospheric Pressure is one preferred method to evaluate the boiling range of a hydrocarbon composition suitable for use in the QCM. Removal of volatile components will alter the boiling range of the hydrocarbon composition. The whole boiling range, from the initial boiling point to the final boiling point, is suitable to evaluate the suitability of the hydrocarbon composition for use in the QCM. However, some boiling ranges are preferred; such as the temperatures at which 70 vol %, 80 vol %, 85 vol %, 90 vol %, and 95 vol % of the hydrocarbon composition have distilled. More preferred boiling ranges include the temperatures at which 40 vol %, 50 vol %, and 60 vol % of the hydrocarbon composition have distilled. Even more preferred boiling ranges include the temperatures at which 20 vol % and 30 vol % have distilled. Most preferred boiling ranges include the initial boiling point and the temperatures at which 5 vol %, 10 vol %, and 15 vol % have distilled. A single temperature at which a certain volume has been distilled is suitable to evaluate suitability for use in the QCM. Combinations of boiling ranges or temperatures at which certain volumes have been distilled are also suitable to evaluate for use in the QCM. Another preferred combination of boiling ranges is the initial boiling point as well as the temperatures at which 5 vol %, 10 vol %, 15 vol %, and 20 vol % distill. An additional preferred combination includes the initial boiling point and the temperatures at which 5 vol %, 10 vol %, 15 vol %, 20 vol %, 30 vol %, and 40 vol % distill. The specified volume percentages chosen are representative of those typically reported in an ASTM D86 distillation and should not be considered limiting to this invention.

EXAMPLES

The following examples are illustrative of exemplary embodiments of the disclosure. In these examples, as well as elsewhere in this application, all ratios, parts, and percentages are by weight unless otherwise indicated. It is intended that these examples are being presented for the purpose of illustration only and are not intended to limit the scope of the invention disclosed herein.

Example 1

In Example 1, a US-sourced E10 gasoline was run on the QCM without evaporating volatile components but with 1 minute of helium sparging. The mass of the fuel prior to sparging was 20.78 g, after sparging the mass reduced to 20.43 g. A stainless steel coated sensor disc (model QSX 304 from Nanoscience Instruments) was used. The experiment was performed with a constant flow rate of 150 microliters/min, temperature was held constant at 21.5° C. Isooctane was run for approximately 5 minutes to ensure a smooth baseline before the gasoline was introduced. When the gasoline was introduced, high frequency oscillations become apparent particularly at the 9th harmonic (FIG. 1). These frequency oscillations are indicative of vapor bubbles forming in the QCM test cell.

Example 2

Figure 2:
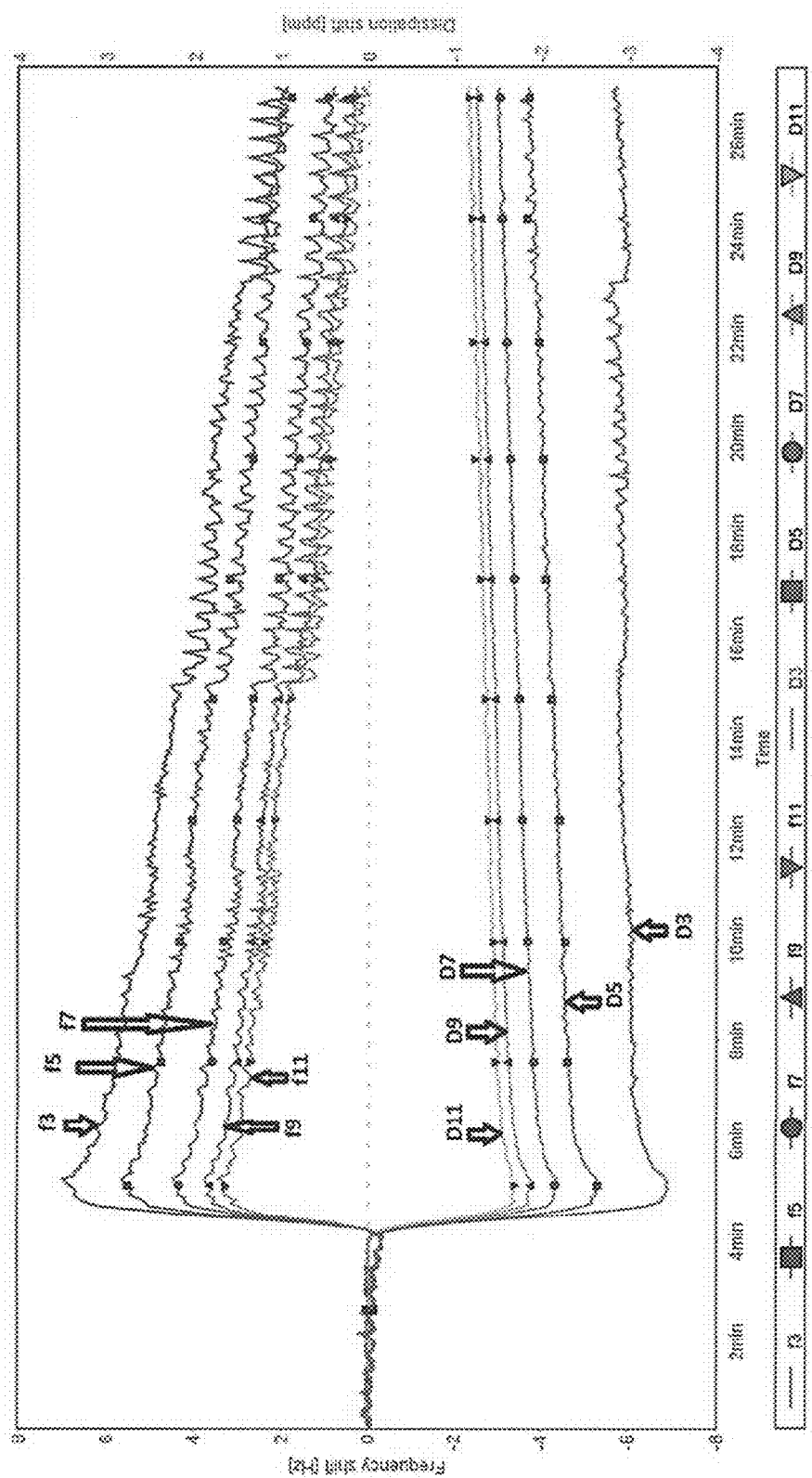

In Example 2, a US-sourced E10 gasoline (from the same lot of gasoline used in Example 1) was run on the QCM without evaporating volatile components or sparging. A stainless steel coated sensor disc (model QSX 304 from Nanoscience Instruments) was used. The experiment was started with a flow rate of 150 microliters/min and temperature was held constant at 21.5° C. Isooctane was run for approximately 4 minutes to ensure a smooth baseline before the gasoline was introduced. At 9 min 18 sec, flow rate was increased to 250 microliters per minute, at 11 min 26 sec the flow rate was reduced to 100 microliters/min, and at 14 min 9 sec the flow rate was increased to 150 microliters/min for the duration of the experiment. After the gasoline was introduced, FIG. 2 shows high frequency oscillations became progressively worse throughout the experiment. The frequency oscillations observed at the 3rd, 5th, 7th, 9th, and 11th harmonics are indicative of vapor bubbles forming in the QCM test cell.

Example 3

Figure 3:
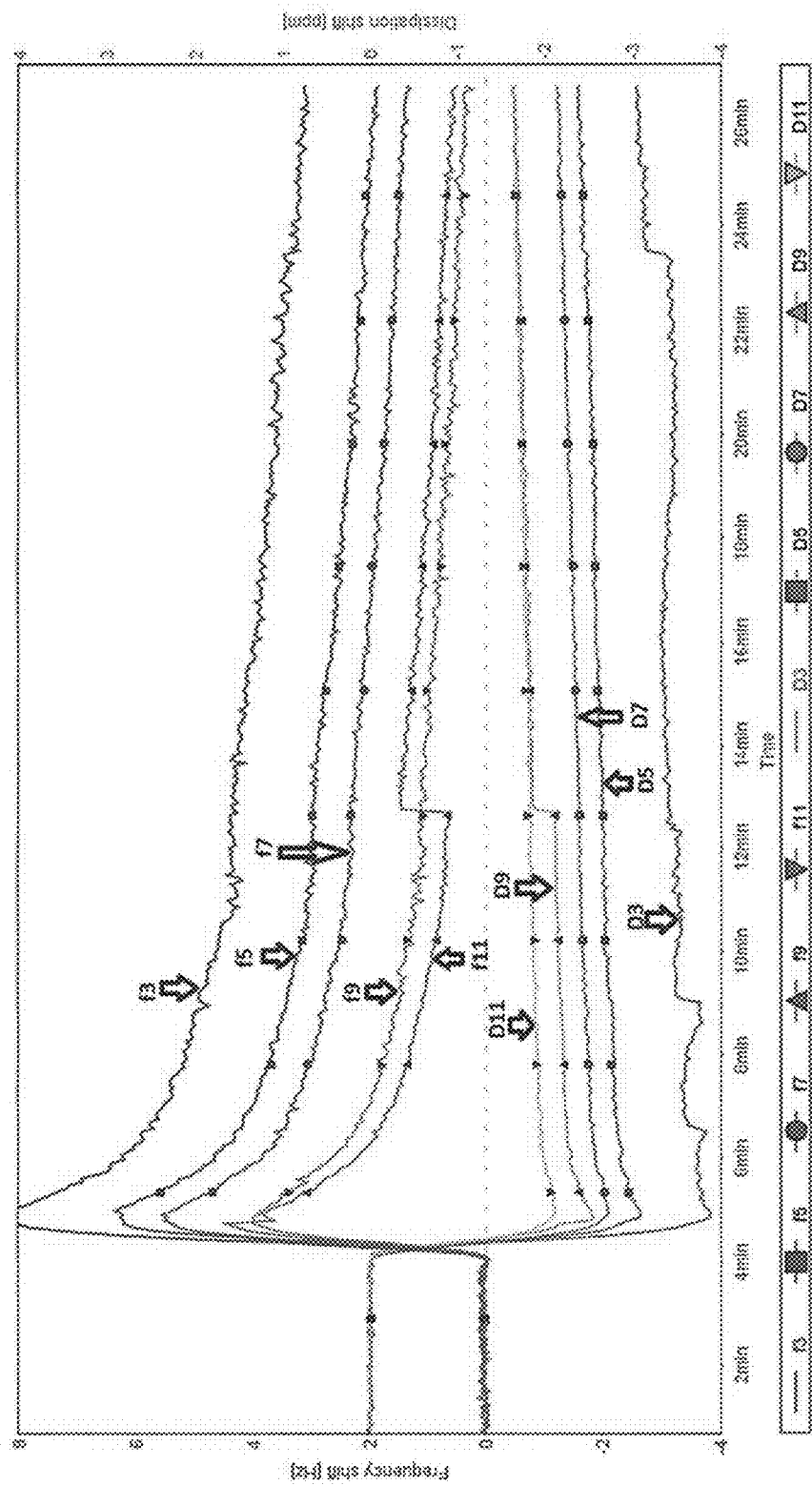

In Example 3, a US-sourced E0 gasoline was run on the QCM without evaporating volatile components or sparging. A stainless steel coated sensor disc (model QSX 304 from Nanoscience Instruments) was used. The experiment was started with a flow rate of 150 microliters/min and temperature was held constant at 21.5° C. Isooctane was run for approximately 4 minutes to ensure a smooth baseline before the E10 gasoline was introduced. At 9 min 18 sec, flow rate was increased to 250 microliters per minute, at 11 min 26 sec the flow rate was reduced to 100 microliters/min, and at 14 min 9 sec the flow rate was increased to 150 microliters/min for the duration of the experiment. After the gasoline was introduced, FIG. 3 shows increased noise in the 3$^{rd}$ harmonic and unexplained frequency spikes in the 9$^{th}$ harmonic.

Example 4

Figure 4:
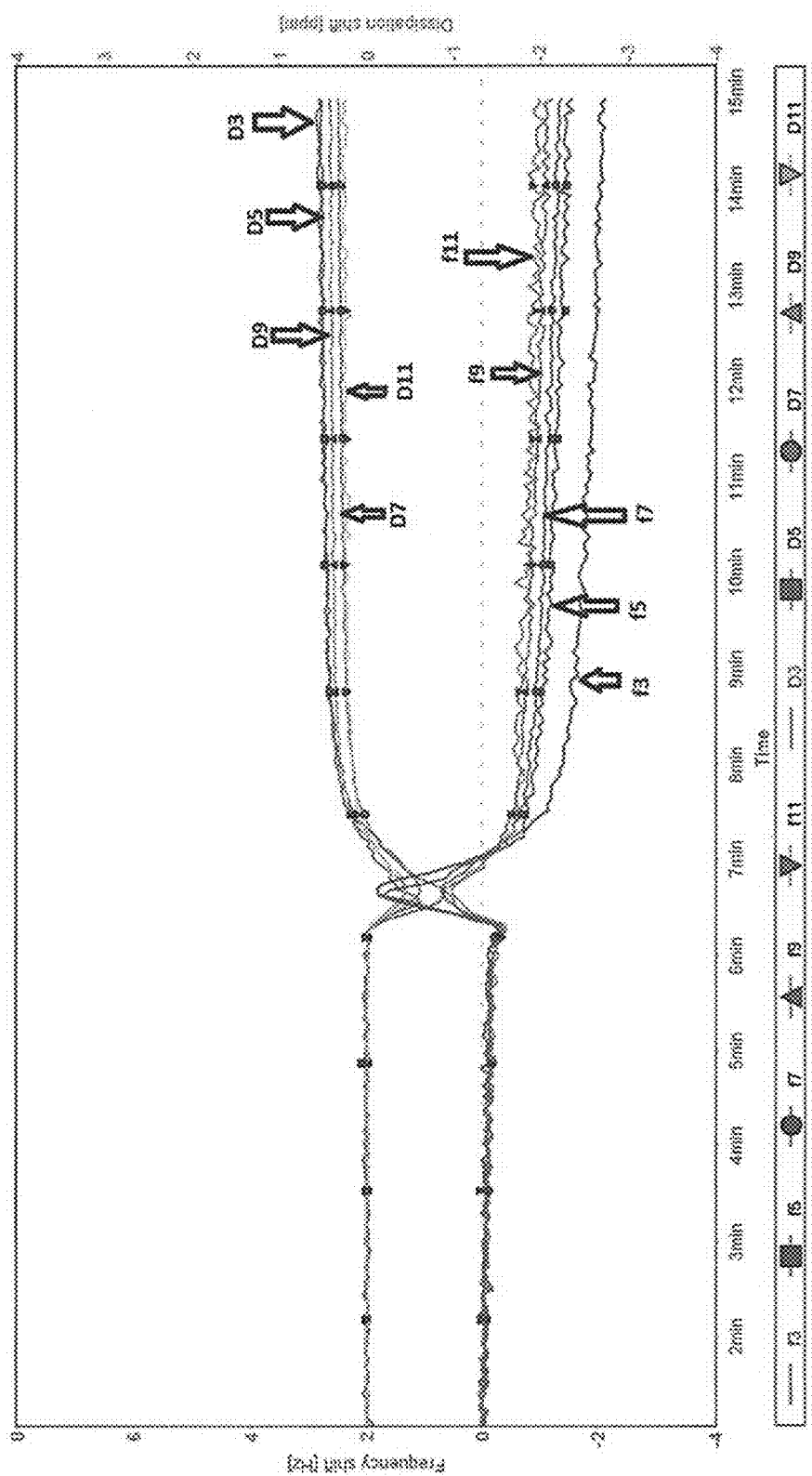
Figure 5:
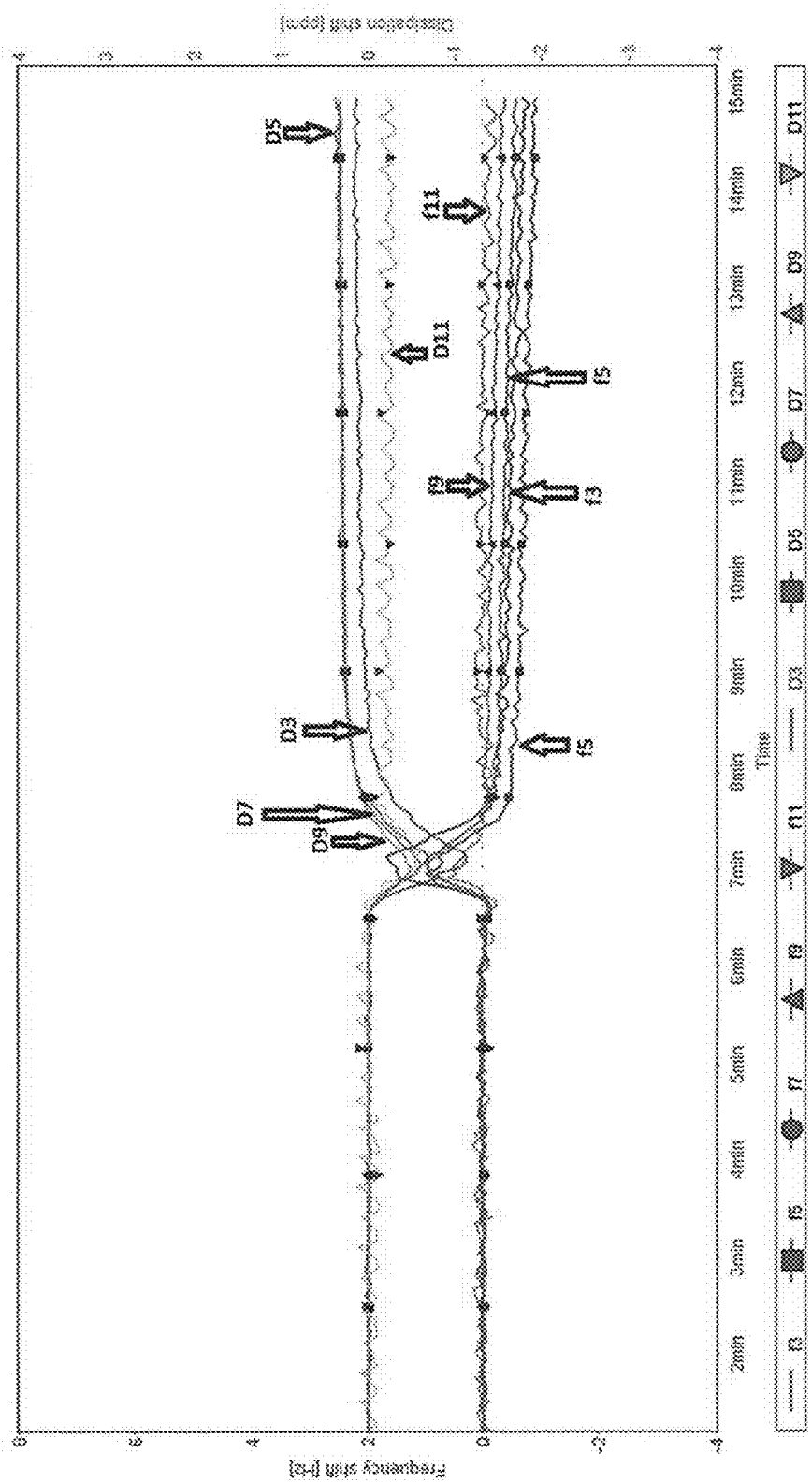
Figure 6:
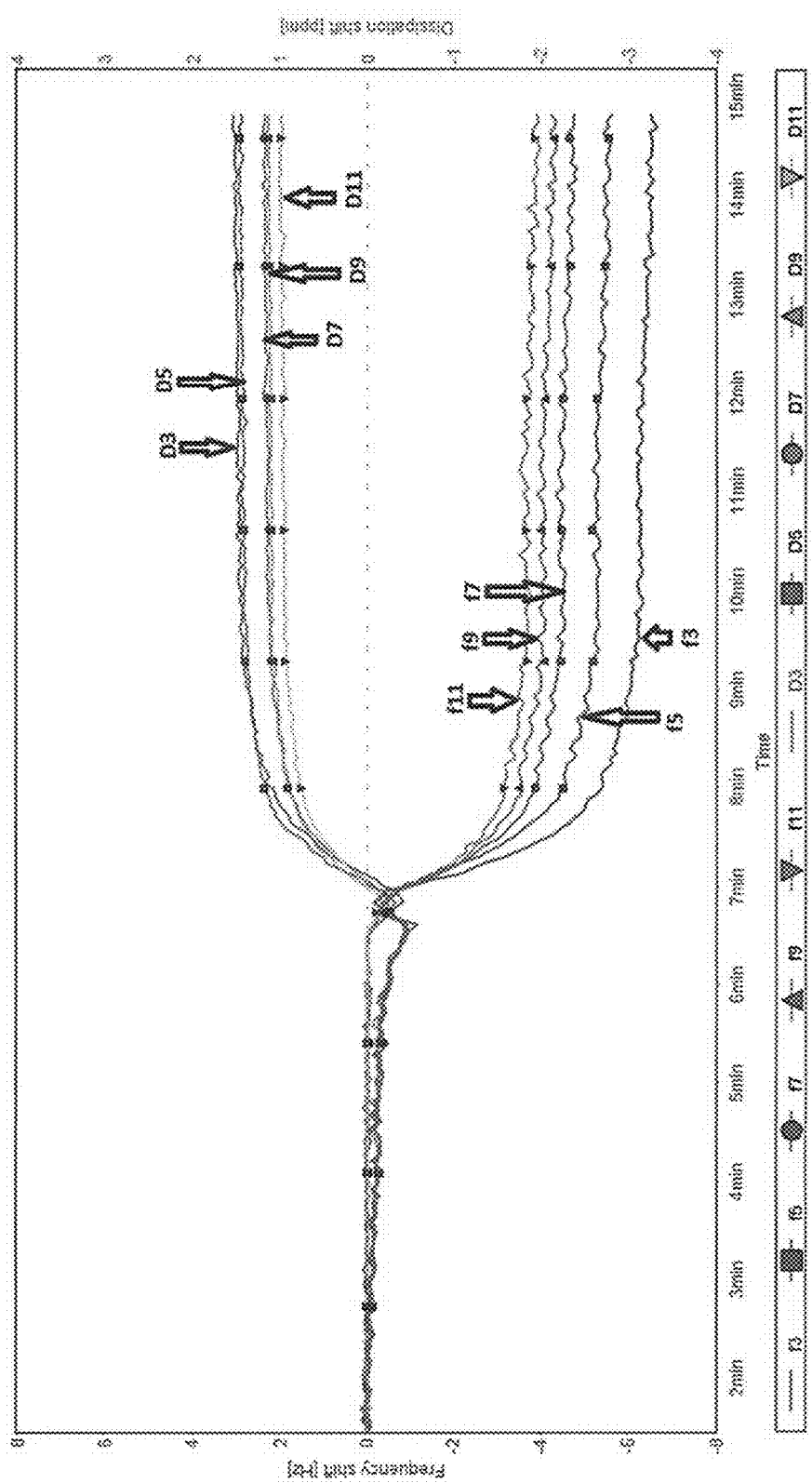

In Example 4, a US-sourced E10 gasoline (from the same lot of gasoline used in Example 1) was bubbled with nitrogen for varying amounts of time to evaporate volatile components. Nitrogen was bubbled through at a rate to create a continuous stream of bubbles in the fluid. The fluids were then sparged with helium for 1 minute immediately prior to QCM analysis. A stainless steel coated sensor disc (model QSX 304 from Nanoscience Instruments) was used. The experiment was started with a flow rate of 150 microliters/min and temperature was held constant at 21.5° C. Isooctane was run for approximately 5 minutes to ensure a smooth baseline before the samples were introduced. Table 1 summarizes mass changes before and after bubbling as well as sparging. After gasoline samples were introduced, FIGS. 4-6 show reduced noise, reduced high frequency oscillations, and reduced frequency spikes. In FIG. 5, increased noise in the dissipation value for the 11$^{th}$ harmonic is noted throughout the entire run. Since this effect is observed through the entire run, the increased noise is not attributed to the gasoline.

TABLE 1

| Sample | Starting Mass (g) | Bubbling Time (min) | Ending Mass (g) | Mass Before Sparging (g) | Mass After Sparging (g) | QCM Plot |
|---|---|---|---|---|---|---|
| E10 - 30 min | 218.46 | 30 | 207.97 | 21.64 | 21.46 | FIG. 4 |
| E10 - 45 min | 219.42 | 45 | 208.16 | 20.62 | 20.46 | FIG. 5 |
| E10 - 90 min | 218.43 | 60 | 199.72 | 21.77 | 21.63 | FIG. 6 |

Example 5

Figure 7:
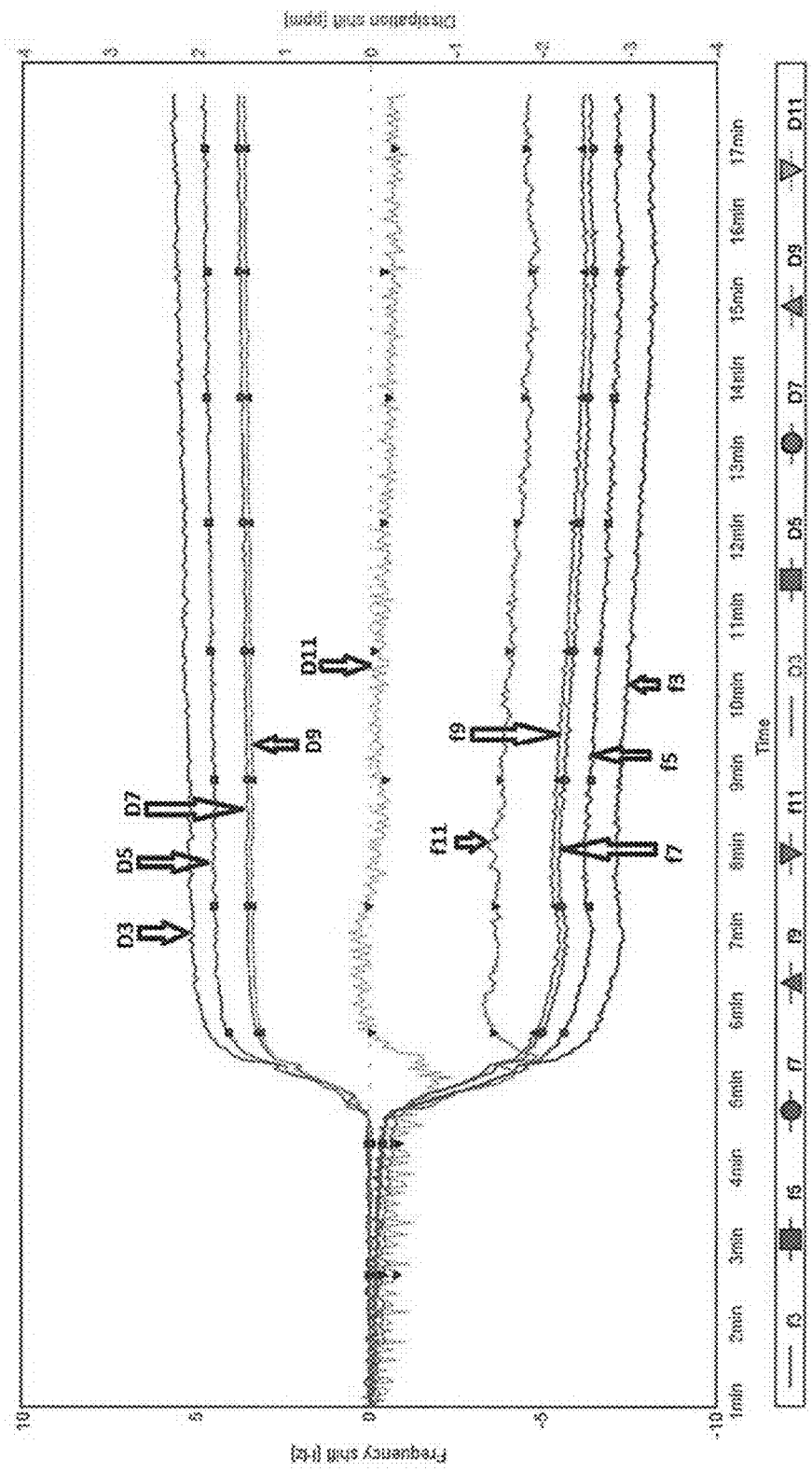
Figure 8:
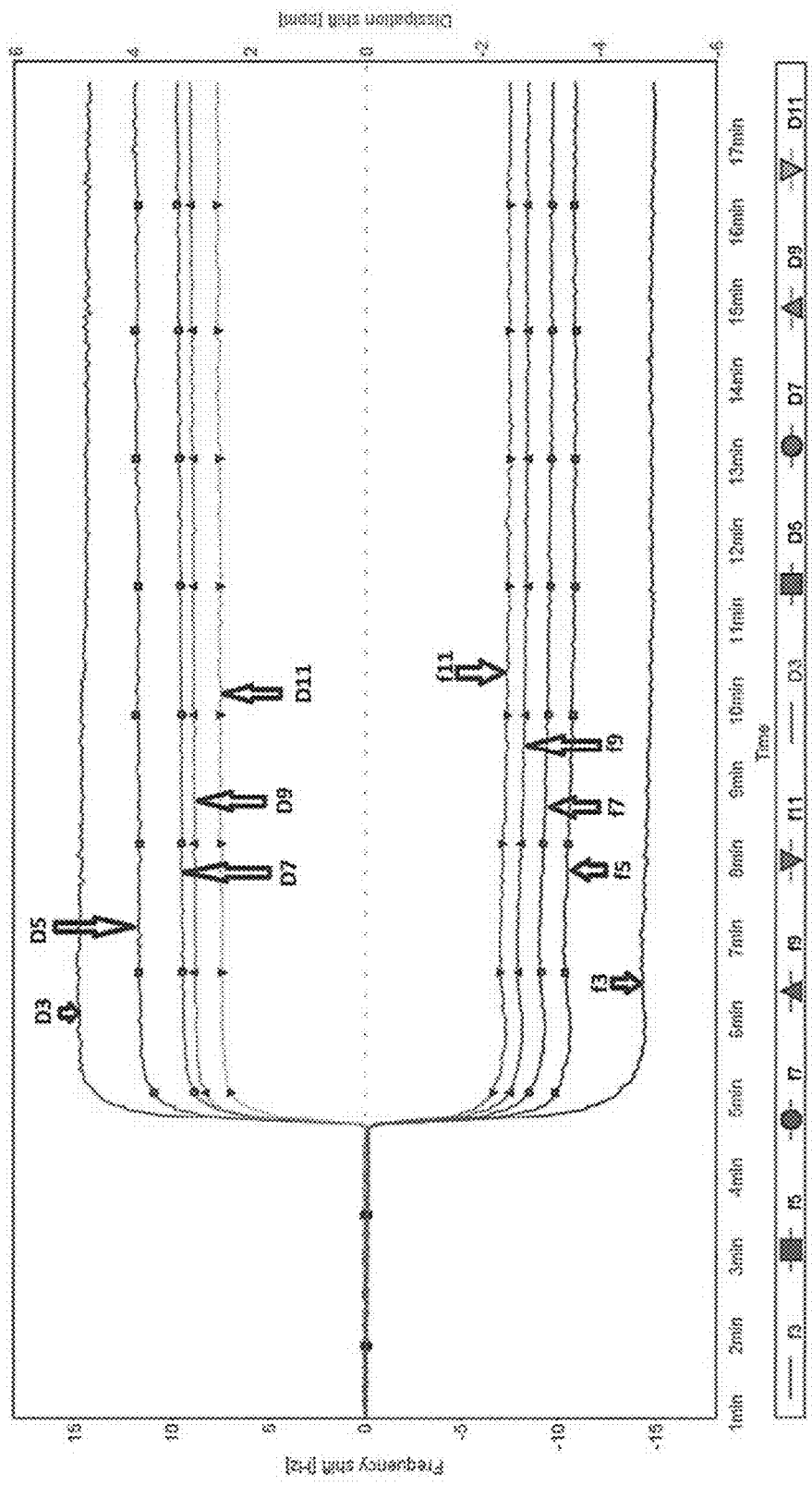
Figure 9:
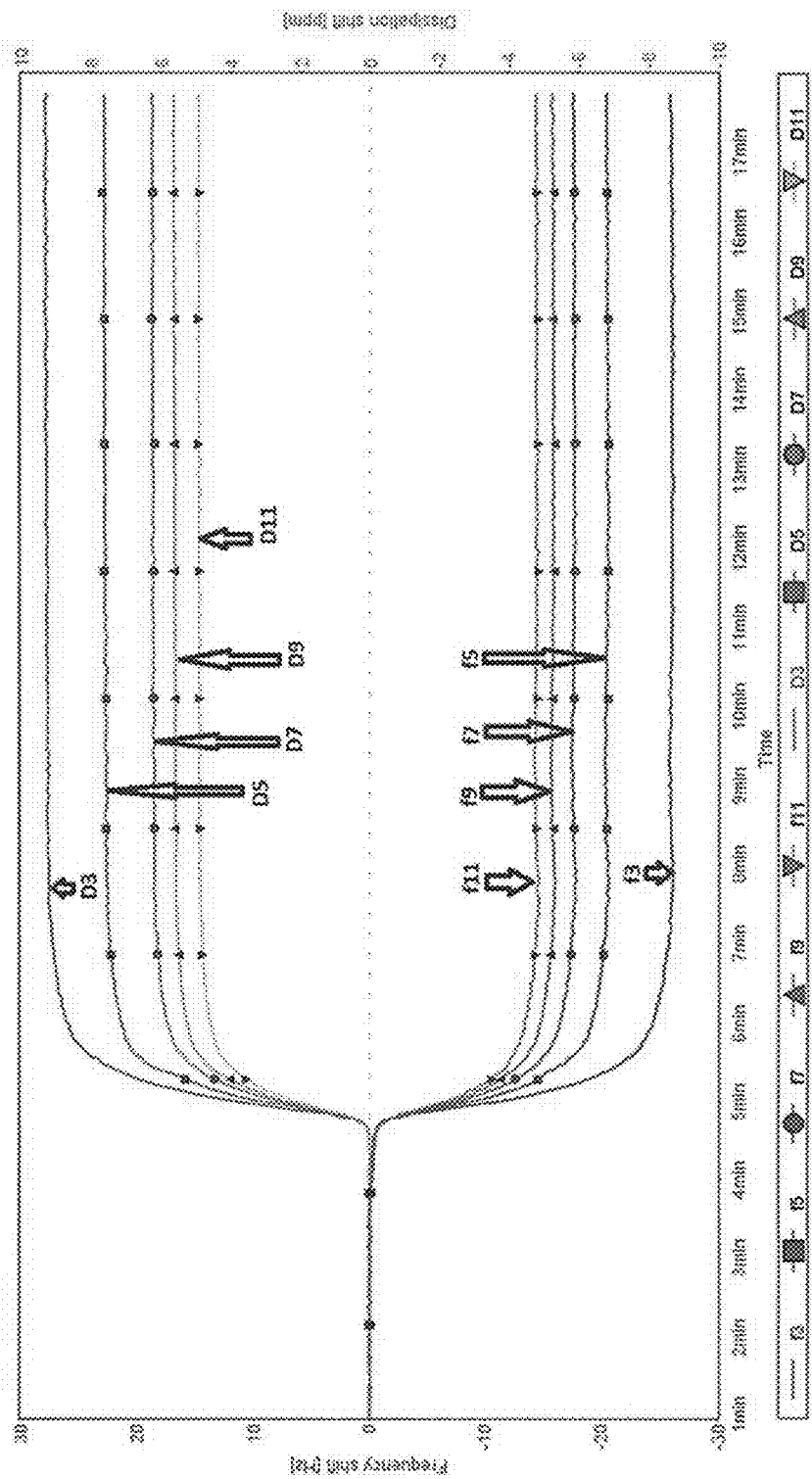

In Example 5, a US-sourced E0 gasoline (from the same lot of gasoline used in Example 3) was bubbled with nitrogen for varying amounts of time amounts of time to evaporate volatile components. Nitrogen was bubbled through at a rate to create a continuous stream of bubbles in the fluid. The fluids were then sparged with helium for 1 minute immediately prior to QCM analysis. Table 2 summarizes mass changes before and after bubbling as well as sparging. A stainless steel coated sensor disc (model QSX 304 from Nanoscience Instruments) was used. The experiment was started with a flow rate of 150 microliters/min and temperature was held constant at 21.5° C. The instrument was run on isooctane for approximately 4 minutes to ensure a smooth baseline before the samples were introduced. After gasoline samples were introduced, FIGS. 7-9 show reduced noise, high frequency oscillations, and frequency spikes. In FIG. 7, increased noise in the dissipation value for the 11$^{th}$ harmonic is noted throughout the entire run. Since this effect is observed through the entire run, the increased noise is not attributed to the gasoline.

TABLE 2

| Sample | Starting Mass (g) | Bubbling Time (min) | Ending Mass (g) | Mass Before Sparging (g) | Mass After Sparging (g) | QCM Plot |
|---|---|---|---|---|---|---|
| E0 - 60 min | 218.78 | 60 | 201.34 | 20.22 | 20.13 | FIG. 7 |
| E0 - 120 min | 219.30 | 120 | 192.72 | 20.54 | 20.50 | FIG. 8 |
| E0 - 180 min | 217.00 | 180 | 176.99 | 20.85 | 21.81 | FIG. 9 |

Example 6

Figure 10:
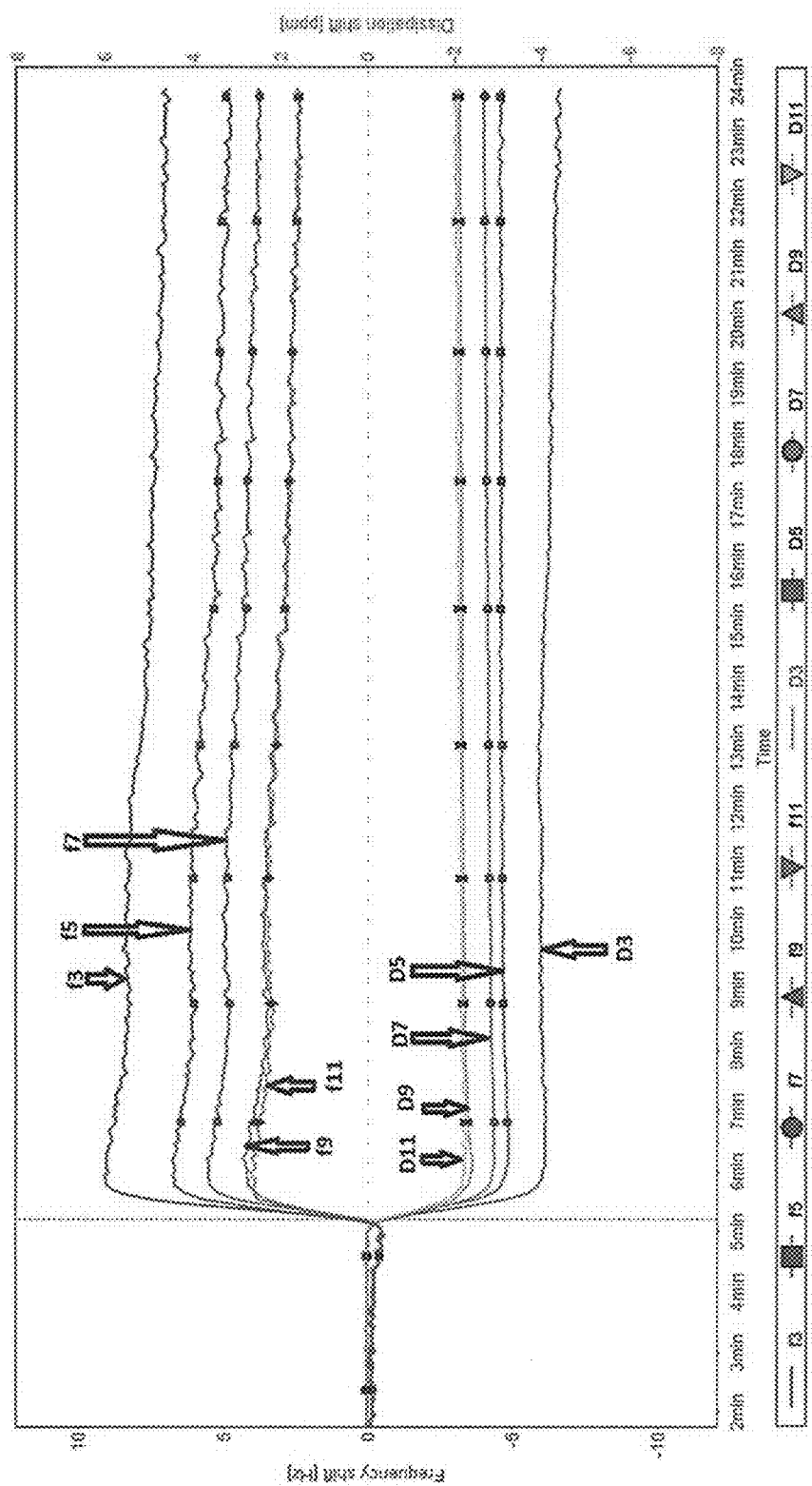

In Example 6, a short path distillation apparatus was set up to distill Tier II EEE reference gasoline. Water was circulated through the condenser. The distillation was performed under ambient temperature but under vacuum. The mass of Tier II EEE reference gasoline was reduced from 202.84 g to 198.14 g. The resulting hydrocarbon composition was then run on the QCM. A stainless steel coated sensor disc (model QSX 304 from Nanoscience Instruments) was used. The experiment was started with a flow rate of 150 microliters/min and temperature was held constant at 21.5° C. The instrument was run on isooctane for approximately 4 minutes to ensure a smooth baseline before the samples were introduced. FIG. 10 shows reduced noise, reduced high frequency oscillations, and reduced frequency spikes.

Example 7

Figure 11:
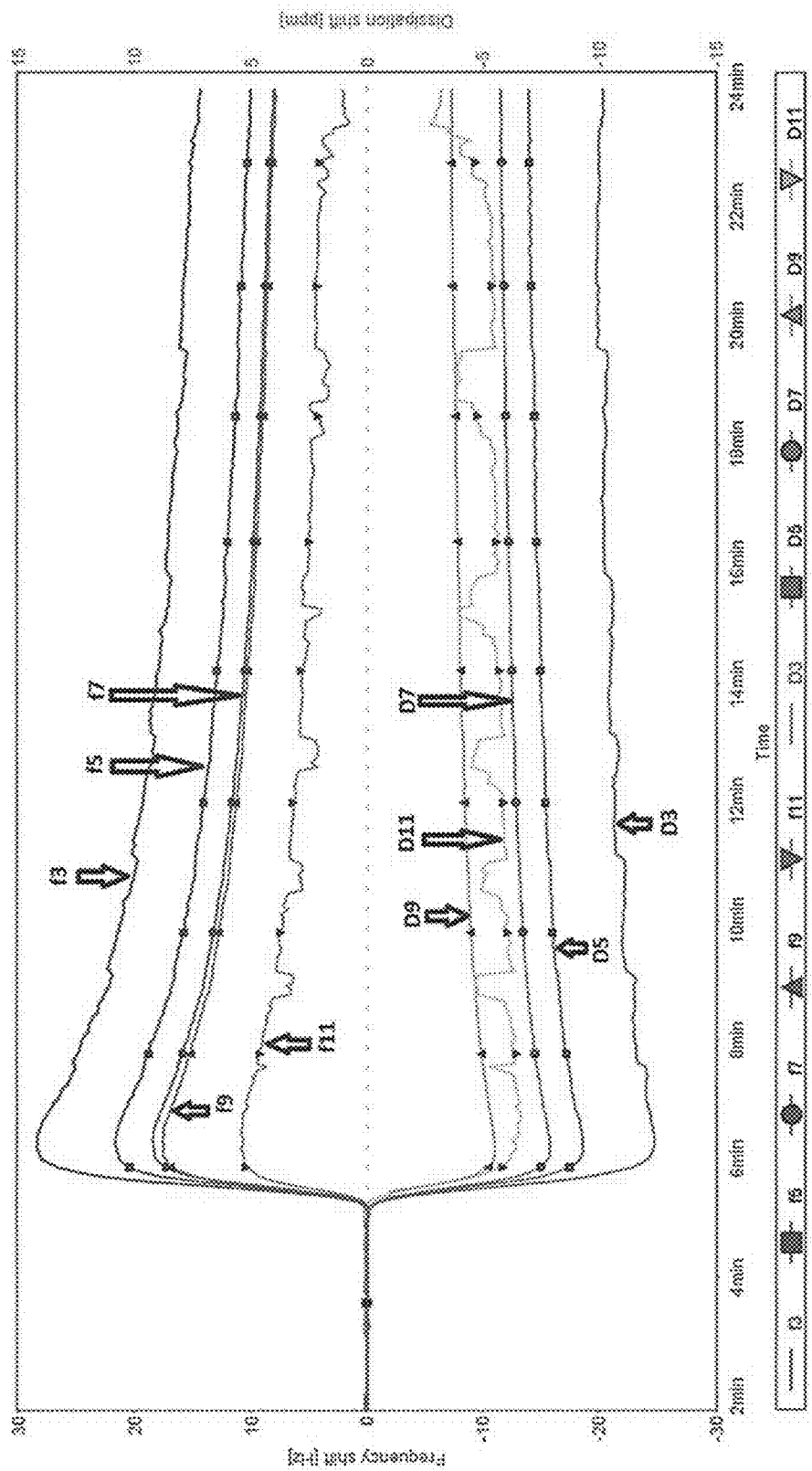

In Example 7, a European sourced Blendstock for Oxygenate Blending (BOB) was run on the QCM without evaporating volatile components or sparging. A stainless steel coated sensor disc (model QSX 304 from Nanoscience Instruments) was used. The experiment was performed with a constant flow rate of 150 microliters/min, temperature was held constant at 21.5° C. The instrument was run on isooctane for approximately 5 minutes to ensure a smooth baseline before the gasoline was introduced. As FIG. 11 shows, noise increased at the 3$^{rd}$ and 11$^{th}$ harmonics. This is evidence of vapors forming the QCM test cell.

Example 8

Figure 12:
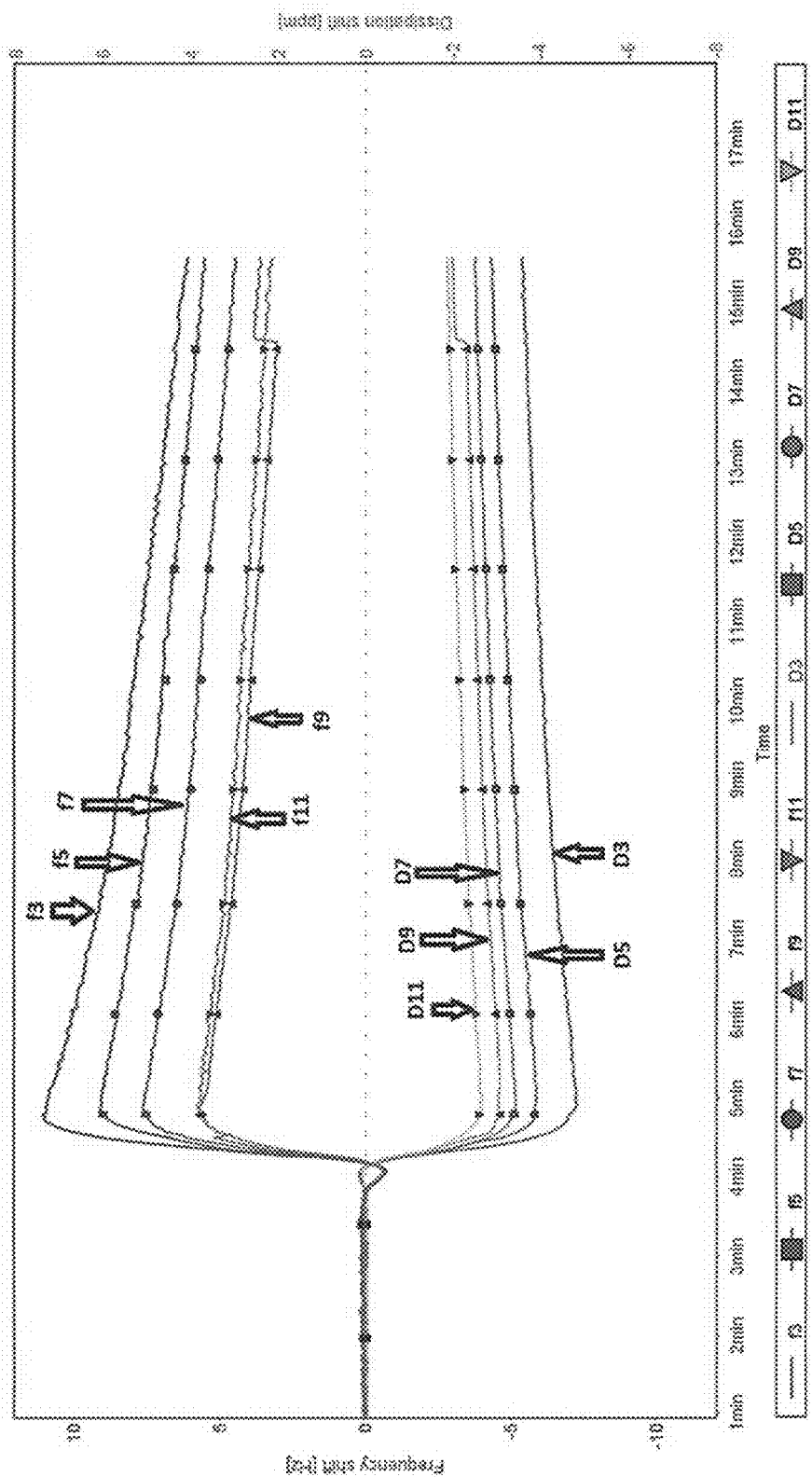

In Example 8, a European sourced Blendstock for Oxygenate Blending (BOB) (from the same lot that was used in Example 7) was bubbled with nitrogen for 60 minutes. Nitrogen was bubbled through at a rate to create a continuous stream of bubbles in the fluid. The mass of gasoline prior to bubbling was 246.44 g, after bubbling the mass was 203.41 g. The fluid was then sparged with helium for 1 minute immediately prior to QCM analysis. The mass prior to sparging was 21.88 g, after sparging the mass was 21.75 g. A stainless steel coated sensor disc (model QSX 304 from Nanoscience Instruments) was used. The experiment was started with a flow rate of 150 microliters/min and temperature was held constant at 21.5° C. The instrument was run on isooctane for approximately 4 minutes to ensure a smooth baseline before the samples were introduced. FIG. 12 shows reduced noise, reduced high frequency oscillations, and reduced frequency spikes.

Example 9

Figure 13:
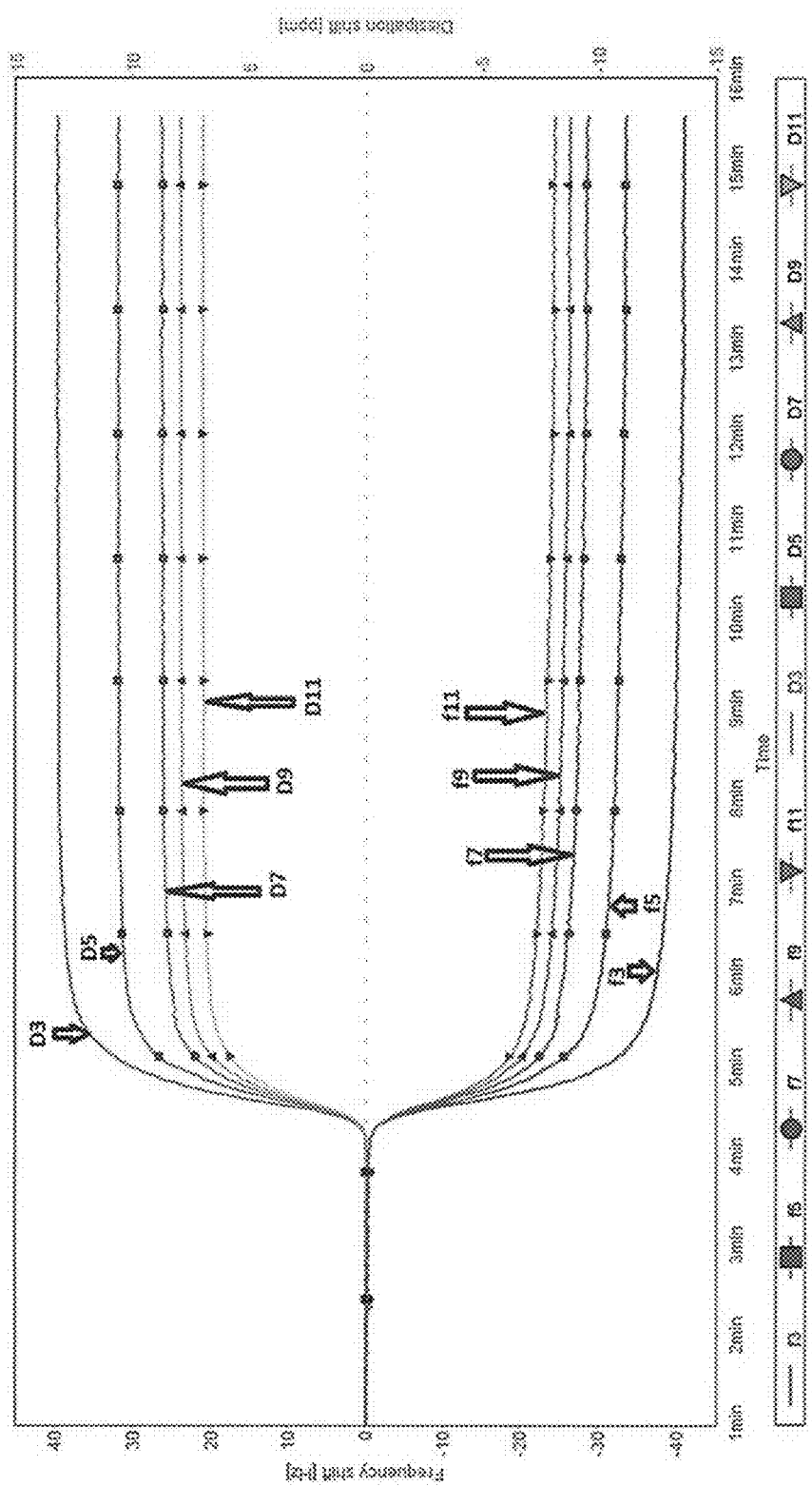

In Example 9, the volatile components present in the same lot of US-sourced E0 gasoline used in Example 3 were removed using rotary evaporation. A round bottom flask containing 95.89 g of E0 gasoline was connected to a rotary evaporator. To prevent bumping, over a 5 minute period the heating bath was increased form ambient temperature to 37° C. and pressure was reduced from atmospheric to 101 Torr. These conditions were held for 10 minutes, the flask was removed from the rotary evaporator. The mass of fuel after rotary evaporation was 72.12 g. A sample of this material (22.48 g) was then helium sparged for 1 minute, the mass after sparging was 22.39 g. The resulting hydrocarbon composition was then run on the QCM. A stainless steel coated sensor disc (model QSX 304 from Nanoscience Instruments) was used. The experiment was started with a flow rate of 150 microliters/min and temperature was held constant at 21.5° C. The instrument was run on isooctane for approximately 4 minutes to ensure a smooth baseline before the samples were introduced. FIG. 13 shows reduced noise, reduced high frequency oscillations, and reduced frequency spikes.

Example 10

Figure 14:
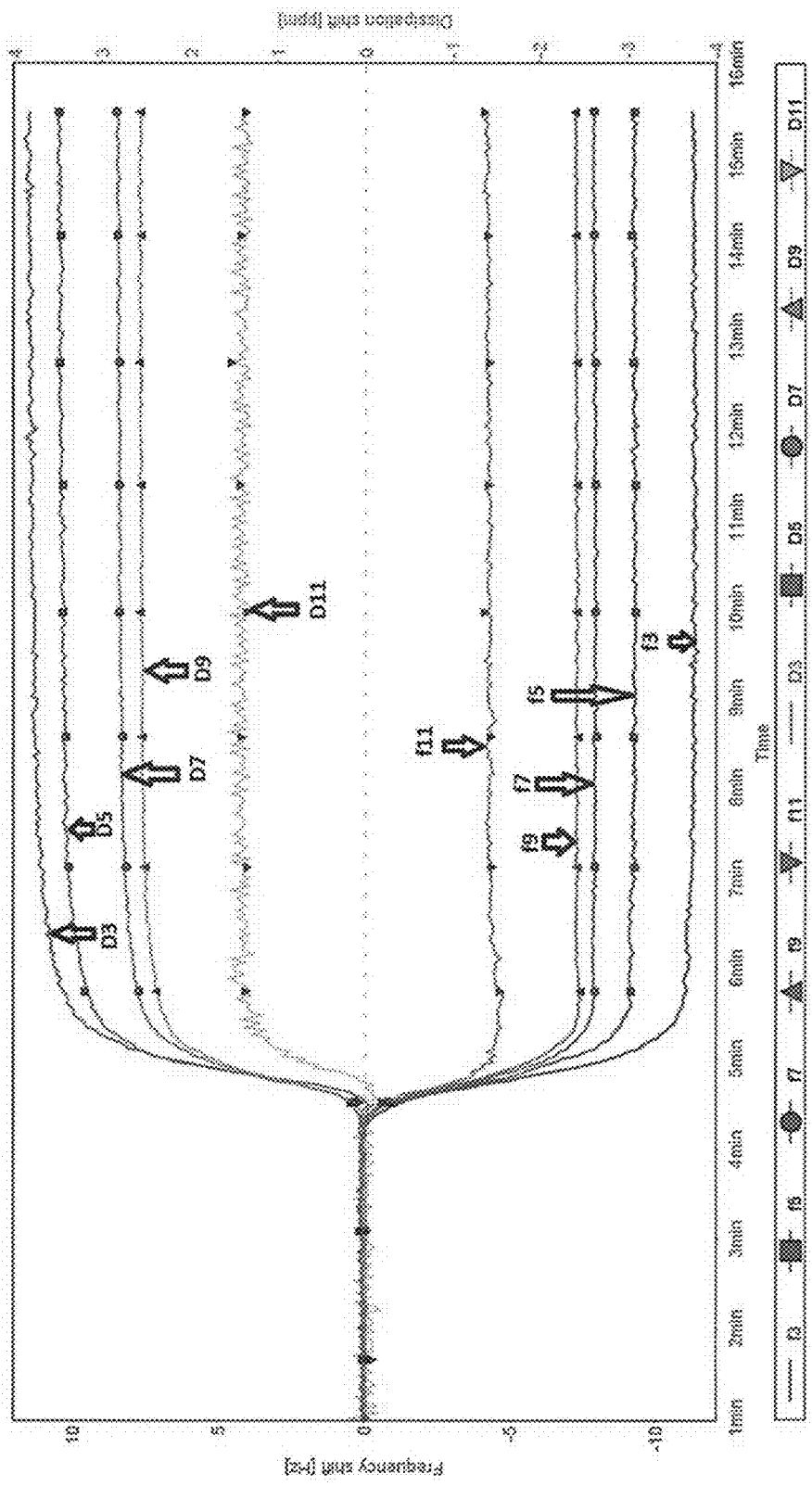

In Example 10, nitrogen was bubbled through the same lot of Tier II EEE reference gasoline used in Example 6 for 60 minutes. Nitrogen was bubbled through at a rate to create a continuous stream of bubbles in the fluid. The mass of the gasoline prior to bubbling was 269.76 g, after bubbling the mass was 229.61 g. Some of the fluid was then sparged with helium for 1 minute immediately prior to QCM analysis. The mass prior to sparging was 23.30 g, after sparging the mass was 23.20 g. A stainless steel coated sensor disc (model QSX 304 from Nanoscience Instruments) was used. The experiment was started with a flow rate of 150 microliters/min and temperature was held constant at 21.5° C. The instrument was run on isooctane for approximately 4 minutes to ensure a smooth baseline before the samples were introduced. FIG. 14 shows reduced noise, reduced high frequency oscillations, and reduced frequency spikes. In FIG. 14, increased noise in the dissipation value for the 11$^{th}$ harmonic is noted throughout the entire run. Since this effect is observed through the entire run, the increased noise is not attributed to the gasoline.

Example 11

Figure 15:
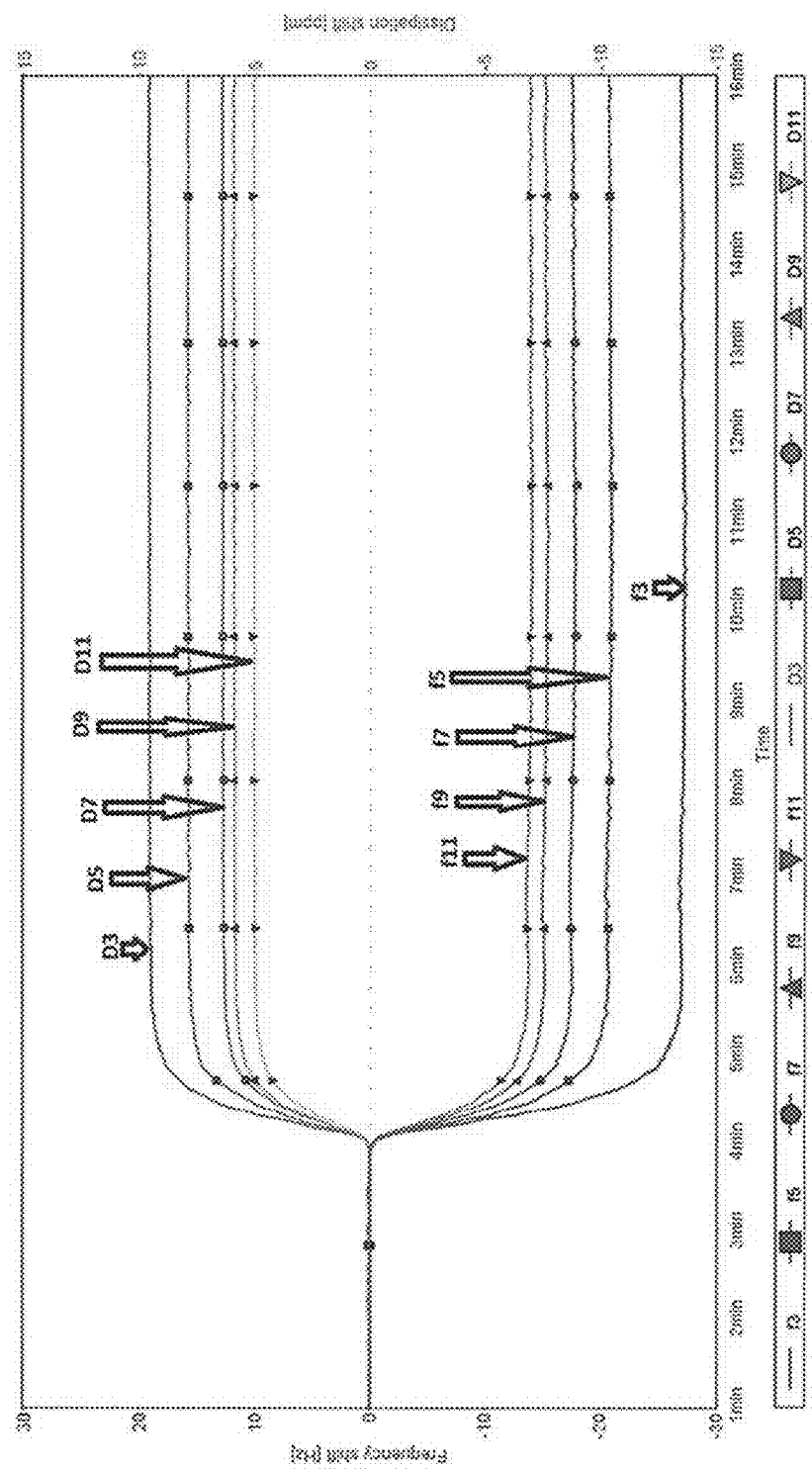

In Example 11, a sample of US-sourced E0 gasoline (from the same lot of gasoline used in Example 3) was left open to the atmosphere in a fume hood for 6 hours. Over this time, the mass of fuel reduced from 274.03 g to 217.02 g. This hydrocarbon composition was run on the QCM without sparging. A stainless steel coated sensor disc (model QSX 304 from Nanoscience Instruments) was used. The experiment was started with a flow rate of 150 microliters/min and temperature was held constant at 21.5° C. The instrument was run on isooctane for approximately 4 minutes to ensure a smooth baseline before the samples were introduced. FIG. 15 shows reduced noise, reduced high frequency oscillations, and reduced frequency spikes.

Example 12

The distillation properties of the US E10 gasoline used in Example 1 was measured with the ASTM D86 distillation method. Table 3 summarizes the results from the E10 gasoline control as well as the changes in boiling range that result from the removal of volatile components after 30, 45, and 90 minutes of bubbling as described in Example 4.

TABLE 3

| Volume % Distilled | Temperature ° C. E10 Gasoline Control | Temperature ° C. E10 30 min. Bubbling | Temperature ° C. E10 45 min. Bubbling | Temperature ° C. E10 90 min. Bubbling |
|---|---|---|---|---|
| 0 (IBP) | 31.1 | 39.6 | 38.1 | 42.1 |
| 5 | 37.6 | 53.3 | 52.9 | 56 |
| 10 | 42.3 | 56.5 | 56.3 | 58.9 |
| 20 | 49.3 | 61.3 | 61.2 | 62.8 |
| 30 | 55.7 | 65.1 | 64.9 | 66.1 |
| 40 | 62.1 | 73.0 | 71.6 | 79.9 |
| 50 | 66.7 | 99.9 | 99.3 | 103.0 |
| 60 | 93 | 113.3 | 113.2 | 115.9 |
| 70 | 114.7 | 128.8 | 128.3 | 131.2 |
| 80 | 134.2 | 147.6 | 147.0 | 149.5 |
| 90 | 157.4 | 172.0 | 171.1 | 171.5 |
| 95 | 177.4 | 193.3 | 193.2 | 193.4 |
| 95.8 (FBP) | 203.9 | 206.6 | 207.3 | 207.8 |

Example 13

The boiling properties of the US E0 gasoline used in Example 3 was measured with the ASTM D86 distillation method. Table 4 summarizes the E0 gasoline control as well as the changes in boiling range that result from the removal of volatile components after 60, 120, and 180 minutes of bubbling as described in Example 5 and allowing 5 to 6 hours of evaporation as described in Example 11.

TABLE 4

| Volume % Distilled | Temperature ° C. E0 Gasoline Control | Temperature ° C. E0 60 min. Bubbling | Temperature ° C. E0 120 min. Bubbling | Temperature ° C. E0 180 min. Bubbling | Temperature ° C. E0 6 hr Evaporation |
|---|---|---|---|---|---|
| 0 (IBP) | 24.2 | 32.8 | 37.5 | 48.9 | 48.2 |
| 5 | 34.2 | 56.2 | 64.7 | 80.4 | 80.7 |

TABLE 4-continued

| Volume % Distilled | Temperature ° C. E0 Gasoline Control | Temperature ° C. E0 60 min. Bubbling | Temperature ° C. E0 120 min. Bubbling | Temperature ° C. E0 180 min. Bubbling | Temperature ° C. E0 6 hr Evaporation |
|---|---|---|---|---|---|
| 10 | 44.5 | 67.3 | 75.8 | 89.5 | 89.6 |
| 20 | 63.2 | 85.6 | 91.7 | 100.3 | 100.2 |
| 30 | 84 | 99.1 | 103.0 | 108.4 | 108.2 |
| 40 | 100.5 | 109.1 | 111.4 | 115.1 | 115.2 |
| 50 | 111.3 | 117 | 119.1 | 122.0 | 122.7 |
| 60 | 120.2 | 125.6 | 127.4 | 130.0 | 130.8 |
| 70 | 130.6 | 137.3 | 138.3 | 141.7 | 142.3 |
| 80 | 147.2 | 153.7 | 154.8 | 157.3 | 158.6 |
| 90 | 169.3 | 175.8 | 176.0 | 177.0 | 180.0 |
| 95 | 188.6 | 202.9 | 199.2 | 200.6 | 211.3 |
| 95.8 (FBP) | 219.1 | 217.9 | 221.7 | 225.0 | 225.6 |

Example 14

The boiling properties of the EEE Tier II gasoline used in Example 6 was measured with the ASTM D86 distillation method. Table 5 summarizes the EEE Tier II gasoline control as well as the changes in boiling range that result from the distillation described in Example 6.

TABLE 5

| Volume % Distilled | Temperature ° C. EEE Tier II Gasoline Control | Temperature ° C. EEE Tier II Distilled |
|---|---|---|
| 0 (IBP) | 30.5 | 33.1 |
| 5 | 44.4 | 49.4 |
| 10 | 51.6 | 55.9 |
| 20 | 61.7 | 67.1 |
| 30 | 72.7 | 80.3 |
| 40 | 88.3 | 95.5 |
| 50 | 102.2 | 106.1 |
| 60 | 110 | 112.1 |
| 70 | 115.6 | 117.9 |
| 80 | 124.4 | 130.1 |
| 90 | 156.1 | 165.1 |
| 95 | 170.5 | 189.1 |
| 95.8 (FBP) | 201.1 | 205.3 |

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values. It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a disclosed range from 1 to 4 also means a range from 1 to 3, 1 to 2, 2 to 4, 2 to 3, and so forth is disclosed herein.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A method of determining the surface activity of a hydrocarbon composition on a metal surface, the method comprising:
   (A) treating a hydrocarbon composition by removing at least a portion of volatile components from the hydrocarbon composition to form a treated hydrocarbon composition, wherein the portion of the volatile components in the hydrocarbon composition is reduced by bubbling a gas through the hydrocarbon composition;

(B) introducing the treated hydrocarbon composition to a quartz crystal microbalance; and (C) measuring the frequency of oscillation of the treated hydrocarbon fluid on a metal surface by the quartz crystal microbalance.

2. The method of claim 1, wherein the gas is selected from an inert or a noble gas.

3. The method of claim 1, wherein the gas includes nitrogen, helium, argon, air, oxygen, or a combination thereof.

4. The method of claim 1, wherein the gas is bubbled through the hydrocarbon composition for at least about 10 minutes.

5. The method of claim 1, wherein the gas is bubbled through the hydrocarbon composition for a time sufficient to reduce one or more of (i) bubble formation in the QCM, (ii) the volatile components in the hydrocarbon composition when measured using the ASTM D86 distillation method, (iii) the mass of the hydrocarbon composition, and/or (iv) frequency spikes and/or noise spikes occurring in the analysis of the treated hydrocarbon composition with the QCM.

6. The method of claim 1, wherein the volatile components are removed by allowing the hydrocarbon composition to evaporate at atmospheric pressure.

7. The method of claim 6, wherein the evaporation of the hydrocarbon composition is sufficient to reduce one or more of (i) the volatile components in the hydrocarbon composition when measured using the ASTM D86 distillation method, (ii) the mass of the hydrocarbon composition, or (iii) frequency spikes and/or noise spikes occurring in the analysis of the treated hydrocarbon composition with the QCM.

8. The method of claim 1, wherein the volatile components are removed by distilling the light ends of the hydrocarbon composition.

9. The method of claim 8, wherein the distilling includes rotary evaporation.

10. The method of claim 8, wherein the distillation of hydrocarbon composition is sufficient to reduce one or more of (i) the volatile components in the hydrocarbon composition when measured using the ASTM D86 distillation method, (ii) the mass of the hydrocarbon composition, or (iii) frequency spikes and/or noise spikes occurring in the analysis of the treated hydrocarbon composition with the QCM.

11. The method of claim 1, further including removing at least a portion of any dissolved gas by degassing the treated hydrocarbon composition.

12. The method of claim 11, wherein the degassing is performed through one or more of helium sparging or vacuum degassing.

13. The method of claim 12, wherein the degassing is an inline degassing.

14. The method of claim 1, wherein the hydrocarbon composition is selected from the group consisting of gasoline, an E0 to an E85 gasoline, a gasoline simulant, an EN 228 compliant gasoline, a standard test fuel or reference fuel, or combinations thereof.

15. The method of claim 1, wherein the hydrocarbon composition includes one or more of reformate, alkylate, FCC, straight run gasoline, or isomerate.

16. The method of claim 1, wherein the removed volatile components include C5 or lower hydrocarbons.

17. The method of claim 1, wherein the hydrocarbon composition includes one or more additives selected from the group consisting of metallic octane boosters, organometallic octane boosters, organic octane boosters, pre-ignition preventers, detergents, dispersants, injector cleanliness additives, corrosion inhibitors, markers, demulsifiers, solvents, carrier fluids, conductivity improvers, cold flow improvers, combustion improvers, friction modifiers, antiwear additives, valve seat recession additives, wax inhibitors, and combinations thereof.

18. The method of claim 1, wherein the treating of the hydrocarbon composition is by bubbling or sparging an inert gas in the hydrocarbon composition or by heating the hydrocarbon composition to remove at least a portion of the volatile components or air or combinations thereof.

* * * * *